United States Patent
Wu et al.

(10) Patent No.: US 11,306,040 B2
(45) Date of Patent: Apr. 19, 2022

(54) HALOGEN-CONTAINING COMPOUND AND USE THEREOF, CATALYST COMPOSITION, AND ETHYLENE OLIGOMERIZATION, TRIMERIZATION AND TETRAMERIZATION METHODS

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(72) Inventors: Hongfei Wu, Beijing (CN); Mingfang Zheng, Beijing (CN); Songshuang Hu, Beijing (CN); Tonglin Li, Beijing (CN); Jun Liu, Beijing (CN); Ke Xu, Beijing (CN); Xiaoqing Wang, Beijing (CN); Feng Pan, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

( * ) Notice: Subject to any disclaimer, the term of this patent is extended or adjusted under 35 U.S.C. 154(b) by 0 days.

(21) Appl. No.: 17/310,069

(22) PCT Filed: Oct. 30, 2019

(86) PCT No.: PCT/CN2019/114395
§ 371 (c)(1),
(2) Date: Jul. 14, 2021

(87) PCT Pub. No.: WO2020/147373
PCT Pub. Date: Jul. 23, 2020

(65) Prior Publication Data
US 2022/0064080 A1    Mar. 3, 2022

(30) Foreign Application Priority Data

Jan. 15, 2019 (CN) .......................... 201910036065.4
Jan. 15, 2019 (CN) .......................... 201910036068.8
Jan. 15, 2019 (CN) .......................... 201910037040.6

(51) Int. Cl.
*C07C 2/36* (2006.01)
*B01J 31/22* (2006.01)
*B01J 31/24* (2006.01)
*C07F 11/00* (2006.01)

(52) U.S. Cl.
CPC ............. *C07C 2/36* (2013.01); *B01J 31/2213* (2013.01); *B01J 31/2409* (2013.01); *C07F 11/00* (2013.01); *B01J 2231/20* (2013.01); *B01J 2531/62* (2013.01); *C07C 2531/14* (2013.01); *C07C 2531/24* (2013.01)

(58) Field of Classification Search
None
See application file for complete search history.

(56) References Cited

U.S. PATENT DOCUMENTS

| 3,676,523 | A | 7/1972 | Mason |
| 3,686,351 | A | 8/1972 | Mason |
| 2010/0137669 | A1 | 6/2010 | Han et al. |
| 2015/0045603 | A1* | 2/2015 | Han ...................... B01J 31/143 585/511 |

FOREIGN PATENT DOCUMENTS

| CN | 1401666 A | 3/2003 |
| CN | 1769270 A | 5/2006 |
| CN | 104169003 A | 11/2014 |

(Continued)

OTHER PUBLICATIONS

English translation of WO2019168249A1, through patents.google.com (Year: 2019).*

(Continued)

*Primary Examiner* — Ali Z Fadhel
(74) *Attorney, Agent, or Firm* — Novick, Kim & Lee, PLLC; Allen Xue

(57) ABSTRACT

A halogen-containing compound as shown in a formula I can be used as a ligand for an ethylene oligomerization catalyst composition. The ethylene oligomerization catalyst composition containing the halogen-containing compound can be used to catalyze ethylene oligomerization, trimerization and tetramerization reactions. As a ligand of a catalyst for ethylene oligomerization, a fluoropolymer can effectively improve the catalytic performance of a catalyst system, and particularly exhibits improved activity and selectivity in an ethylene oligomerization reaction.

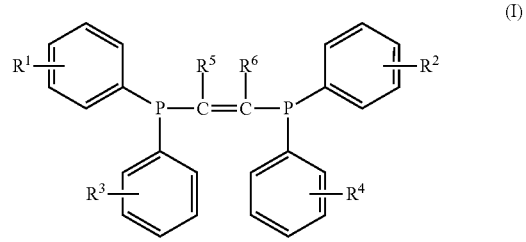

20 Claims, No Drawings

(56) References Cited

FOREIGN PATENT DOCUMENTS

| | | |
|---|---|---|
| CN | 104549510 A | 4/2015 |
| CN | 105562095 A | 5/2016 |
| CN | 105562099 A | 5/2016 |
| CN | 107282126 A | 10/2017 |
| CN | 107282129 A | 10/2017 |
| JP | H1160627 A | 3/1999 |
| WO | 1999001550 A | 1/1999 |
| WO | 1999023096 A | 5/1999 |
| WO | 2004056478 A | 7/2004 |
| WO | 2008119153 A1 | 10/2008 |
| WO | 2009006979 A2 | 1/2009 |

OTHER PUBLICATIONS

Albers et al., "Iron(II) template synthesis of benzannulated triphospha- and triarsamacrocycles", Dalton Trans., 2011, 40, 9525. (Year: 2011).*

Sung-Kwan Kim et. al., Bimetallic Ethylene Tetramerization Catalysts Derived from Chiral DPPDME Ligands: Syntheses, Structural Characterizations, and Catalytic Performance of [(DPPDME)CrCI3]2 (DPPDME = S,S- and R,R-chiraphos and meso-achiraphos), vol. 29, No. 22 Oct. 13, 2010, pp. 5805-5811.

* cited by examiner

HALOGEN-CONTAINING COMPOUND AND USE THEREOF, CATALYST COMPOSITION, AND ETHYLENE OLIGOMERIZATION, TRIMERIZATION AND TETRAMERIZATION METHODS

FIELD OF THE INVENTION

The present invention relates to a halogen-containing compound, and also relates to use of the halogen-containing compound as a ligand of an ethylene oligomerization catalyst composition. The present invention further relates to an ethylene oligomerization catalyst composition, and an ethylene oligomerization, ethylene trimerization and ethylene tetramerization method using the catalyst composition.

BACKGROUND OF THE INVENTION

Ethylene oligomerization is one of the most important reactions in an olefin polymerization industry. An inexpensive small-molecule olefin may be converted into high value-added products, such as 1-octene and 1-hexene, by the oligomerization. The 1-octene and 1-hexene, as important organic raw materials and chemical intermediates, are mainly used in the field of production of high-quality polyethylene (PE). A linear low-density polyethylene (LLDPE) produced by copolymerization of 1-hexene or 1-octene and ethylene may significantly improve various properties of PE, especially the mechanical properties, optical properties, and tear resistance and impact resistance of polyethylene. The resulting product is greatly suitable for a packaging film and agricultural covering-film such as greenhouses and sheds.

Recently, with the continuous development of the polyolefin industry, there is a rapidly increasing demand for α-olefin in the worldwide. Most of the α-olefins are prepared by ethylene oligomerization.

Since the 1970s, the research on polymerization and oligomerization of olefins catalyzed by a transition metal complex has gradually attracted the attention of scientists. Researchers have begun to study novel catalysts and improve existing catalysts to increase the activity of catalysts and the selectivity of catalytic products.

Among the explorations, a nickel-based cationic catalytic system is an earliest, fastest-developing, and relatively concentrated catalytic system, as described in U.S. Pat. Nos. 3,686,351 and 3,676,523, and a Shell's SHOP process based on the patent technology. In the Shell's SHOP process, an O—P bridged ligand is involved, however the catalyst contains a toxic organophosphorus group and has complicated synthesis steps and a poor stability.

Subsequently, researchers further developed an O—O, P—N, P—P and N—N type nickel coordination catalyst, as described in JP11060627, WO9923096, WO991550, CN1401666 and CN1769270. However, the catalysts obtained from the above patents generally have a disadvantage of being prepared in a relatively complex way.

A catalyst with a PNP backbone is disclosed in Patent WO04056478 owned by Sasol Company. In the ethylene tetramerization reaction, the selectivity of a C8 component is about 66 wt %, and the selectivity of a C6 component is about 21 wt %, wherein the content of 1-hexene in the C6 component is only 82%, and the total selectivity of 1-hexene and 1-octene is about 84%.

A catalyst with a PCCP symmetric backbone is disclosed in US20100137669. In the ethylene tetramerization reaction, the catalyst is more stable than the PNP system, but the total selectivity of 1-hexene and 1-octene does not exceed 85%.

In the above-described reaction systems, although by-products such as cycloolefin and a cyclized product existing in the C6 product may be removed by means of separation and purification or the like, it is unfavorable to the economics of the entire process.

SUMMARY OF THE INVENTION

The present invention aims at overcoming the deficiency existing in the prior art, and provides a halogen-containing compound and a catalyst composition containing the halogen-containing compound, wherein the catalyst composition exhibits significantly improved activity and selectivity in an ethylene oligomerization reaction, particularly in ethylene trimerization and tetramerization reactions, and greatly reduces the generation of by-products such as cycloolefin and a cyclized product.

According to a first aspect, the present invention provides a halogen-containing compound, represented by a formula I,

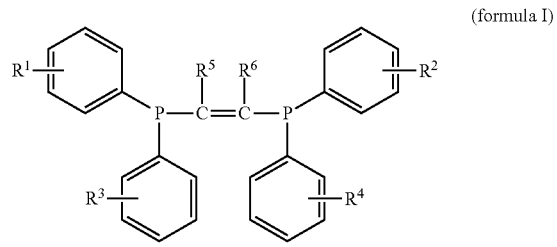

(formula I)

in the formula I, $R^1$, $R^2$, $R^3$ and $R^4$ are the same or different, and each independently halogen; $R^5$ and $R^6$ are the same or different, and each independently hydrogen, $C_1$-$C_{12}$ alkyl, $C_3$-$C_{12}$ cycloalkyl or $C_6$-$C_{20}$ aryl.

According to a second aspect, the present invention provides use of the halogen-containing compound according to the first aspect of the present invention as a ligand of an ethylene oligomerization catalyst composition.

According to a third aspect, the present invention provides an ethylene oligomerization catalyst composition, including at least one halogen-containing compound selected from the first aspect of the present invention, at least one transition metal compound and at least one co-catalyst.

According to a fourth aspect, the present invention provides an ethylene oligomerization method, which includes a step of contacting ethylene with the catalyst composition according to the third aspect of the present invention.

According to a fifth aspect, the present invention provides an ethylene trimerization method, which includes a step of contacting ethylene with the catalyst composition according to the third aspect of the present invention at a temperature of 60° C. or above.

According to a sixth aspect, the present invention provides an ethylene tetramerization method, which includes a step of contacting ethylene with the catalyst composition according to the third aspect of the present invention at a temperature of lower than 60° C.

The halogen-containing polymer according to the present invention, as a ligand of a catalyst for ethylene oligomerization, can effectively improve the catalytic performance of a catalyst system, and particularly exhibits significantly improved catalytic performance in an ethylene oligomerization reaction. The maximum catalyst activity may exceed $4\times10^8$ g·mol(Cr)$^{-1}$·h$^{-1}$, and the total selectivity of 1-hexene and 1-octene exceeds 92 wt %. The content of 1-hexene in a C6 product may reach 95% or above, and the content of 1-octene in a C8 product may reach 98% or above.

In addition, when the catalyst composition of the present invention is used for the oligomerization of ethylene, a high initiation speed is achieved, and the absorption of ethylene can reach the maximum in a short time (within 5 minutes), and maintain for a long time (0.5 hours or above). It is showed that the catalyst composition according to the present invention initiates quickly and has high stability during the polymerization reaction.

Therefore, the catalyst composition according to the present invention has the characteristics of high catalytic activity and high selectivity, and has good industrial application prospects and economic value.

DETAILED DESCRIPTION OF THE EMBODIMENTS

The endpoints and any values of the ranges disclosed herein are not limited to the precise ranges or values, and these ranges or values should be understood to include values close to these ranges or values. For numerical ranges, endpoint values of each range, endpoint values and an individual point value of each range, and individual point values may be combined with each other to obtain one or more new numerical ranges, which should be considered as being specifically disclosed herein.

In the present invention, the term "$C_1$-$C_{12}$ alkyl" includes $C_1$-$C_{12}$ linear alkyl and $C_3$-$C_{12}$ branched alkyl. Specific examples thereof may include, but are not limited to, methyl, ethyl, n-propyl, isopropyl, n-butyl, sec-butyl, isobutyl, tert-butyl, n-pentyl, 2-methylbutyl, 3-methylbutyl, 2,2-dimethylpropyl, n-hexyl, 2-methylpentyl, 3-methylpentyl, 4-methylpentyl, 2,3-dimethylbutyl, 2,2-dimethylbutyl, 3,3-dimethylbutyl, 2-ethylbutyl, n-heptyl, 2-methylhexyl, 3-methylhexyl, 4-methylhexyl, 5-methylhexyl, 2,2-dimethylpentyl, 2,3-dimethylpentyl, 2,4-dimethylpentyl, 3,3-dimethylpentyl, 3,4-dimethylpentyl, 4,4-dimethylpentyl, 2-ethylpentyl, 3-ethylpentyl, n-octyl, 2-methylheptyl, 3-methylheptyl, 4-methylheptyl, 5-methylheptyl, 6-methylheptyl, 2,2-dimethylhexyl, 2,3-dimethylhexyl, 2,4-dimethylhexyl, 2,5-dimethylhexyl, 3,3-dimethylhexyl, 3,4-dimethylhexyl, 3,5-dimethylhexyl, 4,4-dimethylhexyl, 4,5-dimethylhexyl, 5,5-dimethylhexyl, 2-ethylhexyl, 3-ethylhexyl, 4-ethylhexyl, 2-n-propylpentyl, 2-isopropylpentyl, octyl (including various isomers of octyl), decyl (including various isomers of decyl), undecyl (including various isomers of undecyl) and dodecyl (including various isomers of dodecyl).

In the present invention, the term "$C_3$-$C_{12}$ cycloalkyl" includes substituted or unsubstituted cycloalkyl. The substituted cycloalkyl refers to a group in which at least one hydrogen atom bonded to a carbon atom on the ring is replaced by a substituent that may be $C_1$-$C_6$ alkyl, and specific examples of the substituent may include, but are not limited to: methyl, ethyl, n-propyl, isopropyl, n-butyl, sec-butyl, isobutyl, tert-butyl, n-pentyl, isopentyl, tert-pentyl, neopentyl and hexyl (including various isomers of hexyl). Specific examples of the $C_3$-$C_{12}$ cycloalkyl may include, but are not limited to: cyclopropyl, cyclobutyl, cyclopentyl, cyclohexyl, methylcyclohexyl, ethylcyclohexyl, propylcyclohexyl, and butylcyclohexyl.

In the present invention, the term "$C_6$-$C_{20}$ aryl" includes substituted or unsubstituted aryl. The substituted aryl refers to a group in which at least one hydrogen atom on the aromatic ring is replaced by a substituent that may be $C_1$-$C_6$ alkyl and/or a halogen group, and specific examples of the substituent may include, but are not limited to: methyl, ethyl, n-propyl, isopropyl, n-butyl, sec-butyl, isobutyl, tert-butyl, n-pentyl, isopentyl, tert-pentyl, neopentyl, hexyl (including various isomers of hexyl), chlorine, bromine and iodine. Specific examples of the $C_6$-$C_{20}$ aryl may include, but are not limited to: phenyl, naphthyl, tolyl, ethylphenyl, chlorophenyl, or naphthyl.

According to a first aspect, the present invention provides a halogen-containing compound, represented by a formula I,

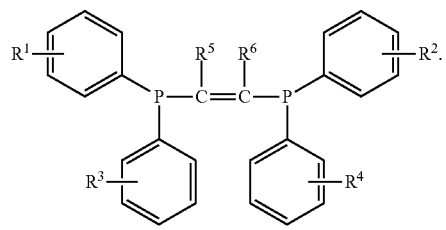

(formula I)

In the formula I, P represents phosphorus.

In the formula I, $R^1$, $R^2$, $R^3$ and $R^4$ are the same or different, and each independently halogen, such as fluorine, chlorine, bromine or iodine. Preferably, $R^2$, $R^3$ and $R^4$ may be the same or different, and each independently chlorine or fluorine. More preferably, all of $R^1$, $R^2$, $R^3$ and $R^4$ are fluorine.

In the formula I, at least one of $R^1$, $R^2$, $R^3$, and $R^4$ is an ortho-substituent. Preferably, all of R', $R^2$, $R^3$ and $R^4$ are an ortho-substituent.

In the formula I, $R^5$ and $R^6$ may be the same or different, and each independently hydrogen, $C_1$-$C_{12}$ alkyl, $C_3$-$C_{12}$ cycloalkyl or $C_6$-$C_{20}$ aryl.

In a preferred embodiment, in the formula I, both $R^5$ and $R^6$ are hydrogen. According to the preferred embodiment, $R^1$, $R^2$, $R^3$ and $R^4$ are each independently preferably chlorine or fluorine, more preferably fluorine.

In a preferred embodiment, in the formula I, $R^5$ and $R^6$ are the same or different, and each independently $C_1$-$C_{12}$ alkyl, $C_3$-$C_{12}$ cycloalkyl or C6-Cao aryl; preferably, in the formula I, $R^5$ and $R^6$ are the same or different, and each independently $C_1$-$C_8$ alkyl, $C_3$-$C_8$ cycloalkyl or $C_6$-$C_{16}$ aryl; more preferably, in the formula I, $R^5$ and $R^6$ are the same or different, and each independently $C_1$-$C_6$ alkyl, $C_3$-$C_6$ cycloalkyl or $C_6$-$C_{12}$ aryl; further preferably, in the formula I, $R^5$ and $R^6$ are the same or different, and each independently methyl, ethyl, n-propyl, isopropyl, n-butyl, tert-butyl, isobutyl, n-pentyl, isopentyl, tert-pentyl, cyclopropyl, cyclobutyl, cyclopentyl, cyclohexyl, phenyl, methylphenyl, ethylphenyl, chlorophenyl or naphthyl; still more preferably, in the formula I, $R^5$ and $R^6$ are the same or different, and each independently tert-butyl, cyclohexyl, phenyl, isopropyl or methyl; particularly preferably, in the formula I, $R^5$ and $R^6$ are the same or different, and each independently tert-butyl, cyclohexyl or methyl. According to the preferred embodiment, $R^1$, $R^2$, $R^3$ and $R^4$ are each independently preferably chlorine or fluorine, more preferably fluorine.

In a preferred embodiment, in the formula I, $R^5$ is hydrogen, and $R^6$ is $C_1$-$C_{12}$ alkyl, $C_3$-$C_{12}$ cycloalkyl or $C_6$-$C_{20}$ aryl; preferably, in the formula I, $R^5$ is hydrogen, and $R^6$ is $C_1$-$C_8$ alkyl, $C_3$-$C_8$ cycloalkyl or $C_6$-$C_{16}$ aryl; more preferably, in the formula I, $R^5$ is hydrogen, and $R^6$ is $C_1$-$C_6$ alkyl, $C_3$-$C_6$ cycloalkyl or $C_6$-$C_{12}$ aryl; further preferably, in the formula I, $R^5$ is hydrogen, and $R^6$ is methyl, ethyl, n-propyl, isopropyl, n-butyl, tert-butyl, isobutyl, n-pentyl, isopentyl, tert-pentyl, cyclopropyl, cyclobutyl, cyclopentyl, cyclohexyl, phenyl, methylphenyl, ethylphenyl, chlorophenyl or naphthyl; still more preferably, in the formula I, $R^5$ is hydrogen, and $R^6$ is tert-butyl, cyclohexyl, phenyl, isopropyl or ethyl; particularly preferably, in the formula I, $R^5$ is hydrogen, and $R^6$ is tert-butyl, cyclohexyl or phenyl. According to the preferred embodiment, R', $R^2$, $R^3$ and $R^4$ are each independently preferably chlorine or fluorine, more preferably fluorine.

The halogen-containing compound according to the present invention may be prepared with reference to the method disclosed in ACS Catalysis, 2013, 3, 2311-2317.

In one embodiment, said halogen-containing compound may be prepared by a method including the steps of: performing a first contact of an alkyne compound represented by a formula IV with a first batch of difluorophenylphosphonium chloride and an organolithium compound at a first temperature; and then adding copper iodide, alkali metal carbonate, and a second batch of difluorophenylphosphonium chloride, and performing a second contact at a second temperature; and separating the halogen-containing compound represented by the formula I from the reaction mixture obtained by the second contact.

(formula IV)

The definitions of $R^5$ and $R^6$ in the formula IV are the same as those in the formula I and will not be described in detail herein.

Said organolithium compound may be a compound represented by a formula V,

(formula V)

In the formula V, $R^{10}$ is $C_1$-$C_6$ alkyl, $C_3$-$C_{12}$ cycloalkyl, $C_7$-$C_{14}$ aralkyl or $C_6$-$C_{12}$ aryl. Specific examples of $R^{10}$ may include, but are not limited to: methyl, ethyl, n-propyl, isopropyl, n-butyl, sec-butyl, isobutyl, tert-butyl, n-pentyl, iso-pentyl, tert-pentyl, neopentyl, n-hexyl, cyclopropyl, cyclopentyl, cyclohexyl, 4-methylcyclohexyl, 4-ethylcyclohexyl, 4-n-propylcyclohexyl, 4-n-butylcyclohexyl, phenylmethyl, phenylethyl, phenyl n-propyl, phenyl n-butyl, phenyl tert-butyl, phenyl isopropyl, phenyl n-pentyl, phenyl n-butyl, phenyl, naphthyl, 4-methylphenyl and 4-ethylphenyl.

Specific examples of the organolithium compound may include, but are not limited to: one or more of ethyl lithium, n-propyl lithium, isopropyl lithium, n-butyl lithium, sec-butyl lithium, tert-butyl lithium, phenyl lithium, 2-naphthyl lithium, 4-butylphenyl lithium, 4-tolyl lithium, cyclohexyl lithium, and 4-butylcyclohexyl lithium.

Preferably, the organolithium compound is n-butyl lithium and/or sec-butyl lithium. More preferably, the organolithium compound is n-butyl lithium.

A molar ratio of the organolithium compound to the alkyne compound represented by the formula IV may be 0.8-1.2:1.

The alkyne compound represented by the formula IV may be mixed with the organolithium compound first, and then to the resulting mixture are added difluorophenylphosphonium chloride. When mixing the alkyne compound and the organolithium compound, it is preferable to add the organolithium compound dropwise into the alkyne compound.

The first contact may be carried out at a temperature of −10° C. to 10° C., preferably −5° C. to 5° C. The duration of the first contact may be 10-60 minutes, preferably 20-40 minutes. The first contact may be carried out in an oxygen-containing heterocyclic compound as a solvent, preferably in tetrahydrofuran.

The alkali metal carbonate is preferably cesium carbonate. The copper iodide and the alkali metal carbonate are used as catalysts in an amount capable of achieving the catalytic function, which may be a catalytic amount.

A molar ratio of the first batch of difluorophenylphosphonium chloride to the second batch of difluorophenylphosphonium chloride may be 1:0.9-1.1, preferably 1:1.

The reaction mixture obtained by the first contact may be mixed with copper iodide and alkali metal carbonate first, and then mixed with the second batch of difluorophenylphosphonium chloride.

The second contact is carried out at a higher temperature than the first contact. Specifically, the second contact may be carried out at a temperature of 60-120° C., preferably 80-100° C.

The halogen-containing compound represented by the formula I may be separated from the reaction mixture obtained by the second contact via conventional methods. For example, the reaction mixture obtained by the second contact may be subjected to solid-liquid separation, and the solvent in the liquid phase produced from the solid-liquid separation is removed. The residue may be subjected to column separation to obtain the halogen-containing compound represented by the formula I.

In one preferred embodiment of the present invention, the halogen-containing compound is selected from compounds represented by formulae II and III,

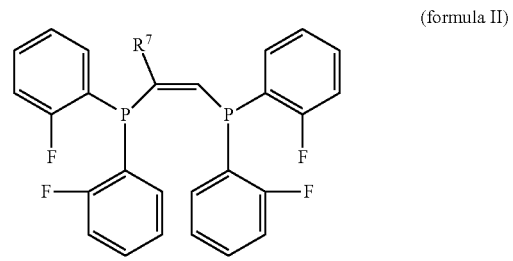

(formula II)

in the formula II, $R^7$ is $C_1$-$C_{12}$ alkyl, $C_3$-$C_{12}$ cycloalkyl or $C_6$-$C_{20}$ aryl;

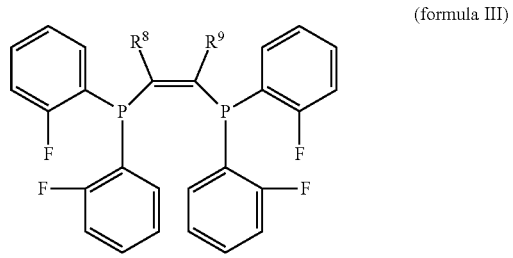

(formula III)

in the formula III, $R^7$ and $R^9$ are the same or different, and each independently $C_1$-$C_{12}$ alkyl, $C_3$-$C_{12}$ cycloalkyl or $C_6$-$C_{20}$ aryl.

In the formulae II and III, IC, $R^8$ and $R^9$ are each independently $C_1$-$C_8$ alkyl, $C_3$-$C_8$ cycloalkyl or $C_6$-$C_{16}$ aryl.

Preferably, in the formulae II and III, $R^7$, $R^8$ and $R^9$ are each independently $C_1$-$C_6$ alkyl, $C_3$-$C_6$ cycloalkyl or $C_6$-$C_{12}$ aryl.

More preferably, in the formulae II and III, $R^7$, $R^8$ and $R^9$ are each independently methyl, ethyl, n-propyl, isopropyl, n-butyl, tert-butyl, isobutyl, n-pentyl, isopentyl, tert-pentyl, cyclopropyl, cyclobutyl, cyclopentyl, cyclohexyl, phenyl, methylphenyl, ethylphenyl, chlorophenyl or naphthyl.

Further preferably, in the formulae II and III, $R^7$, $R^8$ and $R^9$ are each independently tert-butyl, cyclohexyl, phenyl, isopropyl or ethyl.

Still more preferably, in the formula II, $R^7$ is tert-butyl, cyclohexyl or phenyl.

Yet still more preferably, in the formula III, $R^7$ and $R^9$ are each independently tert-butyl, cyclohexyl or methyl.

The halogen-containing compound according to the present invention is particularly suitable as a ligand of a catalyst for ethylene oligomerization. In the case that the ligand of the catalyst contains the halogen-containing compound, the catalyst has significantly improved catalytic performance.

According to a second aspect, the present invention provides use of the halogen-containing compound according to the first aspect of the present invention as a ligand of an ethylene oligomerization catalyst composition.

The halogen-containing compound according to the present invention may be used in combination with a transition metal compound and a co-catalyst commonly used in ethylene oligomerization.

In one preferred embodiment, the catalyst composition contains the transition metal compound, the co-catalyst and the halogen-containing compound.

A transition metal element in the transition metal compound may be chromium, molybdenum, iron, titanium, zirconium or nickel. Accordingly, the transition metal compound may be at least one selected from the group consisting of a chromium compound, a molybdenum compound, an iron compound, a titanium compound, a zirconium compound, and a nickel compound.

The transition metal compound may be at least one selected from the group consisting of transition metal acetylacetonate, transition metal carboxylate, and a complex of a transition metal and tetrahydrofuran.

The transition metal compound is preferably at least one selected from the group consisting of chromium acetylacetonate, chromium isooctanoate, tris(tetrahydrofuran)chromium trichloride, and bis(tetrahydrofuran)chromium dichloride.

The molar ratio of the halogen-containing compound to the transition metal compound may be 1:0.1-10, for example: 1:0.1, 1:0.2, 1:0.3, 1:0.4, 1:0.5, 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

Preferably, the molar ratio of the halogen-containing compound to the transition metal compound is 1:0.25-2. More preferably, the molar ratio of the halogen-containing compound to the transition metal compound is 1:0.5-2. Further preferably, the molar ratio of the halogen-containing compound to the transition metal compound is 1:0.5-1. Still more preferably, the molar ratio of the halogen-containing compound to the transition metal compound is 1:0.5-0.8.

The co-catalyst may be an aluminum-containing co-catalyst. Preferably, the co-catalyst is an organoaluminum compound. More preferably, the co-catalyst is at least one selected from the group consisting of alkyl aluminum, alkoxy aluminum and alkyl aluminum halide. Further preferably, the co-catalyst is at least one selected from the group consisting of methylaluminoxane, trimethylaluminum, triethylaluminum, triisobutylaluminum, tri-n-hexylaluminum, tri-n-octylaluminum, aluminium diethyl monochloride, aluminium ethyl dichloride, ethylaluminoxane and modified methylaluminoxane. Still more preferably, the co-catalyst is at least one selected from the group consisting of modified methylaluminoxane, methylaluminoxane and triethylaluminum. Particularly preferably, the co-catalyst is modified methylaluminoxane. In the present invention, "modified methylaluminoxane" refers to methylaluminoxane which is modified with an alkyl group, for example, butyl modified methylaluminoxane. The modified methylaluminoxane may be modified methylaluminoxane purchased from Akzo Nobel.

The molar ratio of the halogen-containing compound to the co-catalyst may be 1:1-1000. Preferably, the molar ratio of the halogen-containing compound to the co-catalyst is 1:10-700. More preferably, the molar ratio of the halogen-containing compound to the co-catalyst is 1:100-500, for example: 1:100, 1:105, 1:110, 1:115, 1:120, 1:125, 1:130, 1:135, 1:140, 1:145, 1:150, 1:155, 1:160, 1:165, 1:170, 1:175, 1:180, 1:185, 1:190, 1:195, 1:200, 1:205, 1:210, 1:215, 1:220, 1:225, 1:230, 1:235, 1:240, 1:245, 1:250, 1:255, 1:260, 1:265, 1:270, 1:275, 1:280, 1:285, 1:290, 1:295, 1:300, 1:305, 1:310, 1:315, 1:320, 1:325, 1:330, 1:335, 1:340, 1:345, 1:350, 1:355, 1:360, 1:365, 1:370, 1:375, 1:380, 1:385, 1:390, 1:395, 1:400, 1:405, 1:410, 1:415, 1:420, 1:425, 1:430, 1:435, 1:440, 1:445, 1:450, 1:455, 1:460, 1:465, 1:470, 1:475, 1:480, 1:485, 1:490, 1:495 or 1:500.

Further preferably, the molar ratio of the halogen-containing compound to the co-catalyst is 1:150-300. Still more preferably, the molar ratio of the halogen-containing compound to the co-catalyst is 1:200-280.

According to a third aspect, the present invention provides an ethylene oligomerization catalyst composition. The composition contains at least one halogen-containing compound selected from the first aspect of the present invention, at least one transition metal compound and at least one co-catalyst. The halogen-containing compound and the preparation method thereof have been described above, and will not be described in detail here.

The molar ratio of the halogen-containing compound to the transition metal compound may be 1:0.1-10, for example: 1:0.1, 1:0.2, 1:0.3, 1:0.4, 1:0.5, 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

Preferably, the molar ratio of the halogen-containing compound to the transition metal compound is 1:0.25-2. More preferably, the molar ratio of the halogen-containing compound to the transition metal compound is 1:0.5-2.

Further preferably, the molar ratio of the halogen-containing compound to the transition metal compound is 1:0.5-1. Still more preferably, the molar ratio of the halogen-containing compound to the transition metal compound is 1:0.5-0.8.

The co-catalyst may be an aluminum-containing co-catalyst. Preferably, the co-catalyst is an organoaluminum compound. More preferably, the co-catalyst is at least one selected from the group consisting of alkyl aluminum, alkoxy aluminum and alkyl aluminum halide. Further preferably, the co-catalyst is at least one selected from the group consisting of methylaluminoxane, trimethylaluminum, triethylaluminum, triisobutylaluminum, tri-n-hexylaluminum, tri-n-octylaluminum, aluminium diethyl monochloride, aluminium ethyl dichloride, ethylaluminoxane and modified methylaluminoxane. Still more preferably, the co-catalyst is at least one selected from the group consisting of modified methylaluminoxane, methylaluminoxane and triethylaluminum. Particularly preferably, the co-catalyst is modified methylaluminoxane.

The molar ratio of the halogen-containing compound to the co-catalyst may be 1:1-1000. Preferably, the molar ratio of the halogen-containing compound to the co-catalyst is 1:10-700. More preferably, the molar ratio of the halogen-containing compound to the co-catalyst is 1:100-500, for example: 1:100, 1:105, 1:110, 1:115, 1:120, 1:125, 1:130, 1:135, 1:140, 1:145, 1:150, 1:155, 1:160, 1:165, 1:170, 1:175, 1:180, 1:185, 1:190, 1:195, 1:200, 1:205, 1:210, 1:215, 1:220, 1:225, 1:230, 1:235, 1:240, 1:245, 1:250, 1:255, 1:260, 1:265, 1:270, 1:275, 1:280, 1:285, 1:290, 1:295, 1:300, 1:305, 1:310, 1:315, 1:320, 1:325, 1:330, 1:335, 1:340, 1:345, 1:350, 1:355, 1:360, 1:365, 1:370, 1:375, 1:380, 1:385, 1:390, 1:395, 1:400, 1:405, 1:410, 1:415, 1:420, 1:425, 1:430, 1:435, 1:440, 1:445, 1:450, 1:455, 1:460, 1:465, 1:470, 1:475, 1:480, 1:485, 1:490, 1:495 or 1:500.

Further preferably, the molar ratio of the halogen-containing compound to the co-catalyst is 1:150-300. Still more preferably, the molar ratio of the halogen-containing compound to the co-catalyst is 1:200-280.

According to a fourth aspect, the present invention provides an ethylene oligomerization method. The method includes a step of contacting ethylene with the catalyst composition according to the third aspect of the present invention.

According to the ethylene oligomerization method of the present invention, the contacting is preferably carried out in at least one organic solvent. The organic solvent is a solvent capable of dissolving an oligomerization product, and may be at least one selected from the group consisting of an alkane, a cycloalkane and an aromatic hydrocarbon, preferably at least one selected from the group consisting of $C_6$-$C_{12}$ alkane, $C_6$-$C_{12}$ cycloalkane, and $C_6$-$C_{12}$ aromatic hydrocarbon. Specific examples of the organic solvent may include, but are not limited to: hexane, 2-methylpentane, 3-methylpentane, 2,3-dimethylbutane, cyclohexane, methylcyclopentane, heptane, 2-methylhexane, 3-m ethylhexane, methylcyclohexane, 2-ethylpentane, 3-ethylpentane, 2,3-dimethylpentane, 2,4-dimethylpentane, octane, 2-methylheptane, 3-methylheptane, 4-methylheptane, 2,3-dimethylhexane, 2,4-dimethylhexane, 2,5-dimethylhexane, 3-ethylhexane, 2,2,3-trim ethylpentane, 2,3,3-trim ethylpentane, 2,4,4-trimethylpentane, 2-methyl-3-ethylpentane, nonane, 2-methyloctane, 3-methyloctane, 4-methyloctane, 2,3-dimethylheptane, 2,4-dimethylheptane, 3-ethylheptane, 4-ethylheptane, 2,3,4-trimethylhexane, 2,3,5-trimethylhexane, 2,4,5-trimethylhexane, 2,2,3-trimethylhexane, 2,2,4-trimethylhexane, 2,2,5-trimethylhexane, 2,3,3-trimethylhexane, 2,4,4-trimethylhexane, 2-methyl-3-ethylhexane, 1-methyl-4-ethylhexane, 3-methyl-3-ethylhexane, 3-methyl-4-ethylhexane, 3,3-diethylpentane, 1-methyl-2-ethylcyclohexane, 1-methyl-3-ethylcyclohexane, 1-methyl-4-ethylcyclohexane, n-propylcyclohexane, isopropylcyclohexane, trimethylcyclohexane (including various isomers of trimethylcyclohexane, such as 1,2,3-trimethylcyclohexane, 1,2,4-trimethylcyclohexane, 1,2,5-trimethylcyclohexane, 1,3,5-trimethylcyclohexane), decane, 2-methylnonane, 3-methylnonane, 4-methylnonane, 5-methylnonane, 2,3-dimethyloctane, 2,4-dimethyloctane, 3-ethyloctane, 4-ethyloctane, 2,3,4-trimethylheptane, 2,3,5-trimethylheptane, 2,3,6-trimethylheptane, 2,4,5-trimethylheptane, 2,4,6-trimethylheptane, 2,2,3-trimethylheptane, 2,2,4-trimethylheptane, 2,2,5-trimethylheptane, 2,2,6-trimethylheptane, 2,3,3-trimethylheptane, 2,4,4-trimethylheptane, 2-methyl-3-ethylheptane, 2-methyl-4-ethylheptane, 2-methyl-5-ethylheptane, 3-methyl-3-ethylheptane, 4-methyl-3-ethylheptane, 5-methyl-3-ethylheptane, 4-methyl-4-ethylheptane, 4-propylheptane, 3,3-diethylhexane, 3,4-diethylhexane, 2-methyl-3,3-diethylpentane, 1,2-diethylcyclohexane, 1,3-diethylcyclohexane, 1,4-diethylcyclohexane, n-butylcyclohexane, isobutylcyclohexane, tert-butylcyclohexane, tetramethylcyclohexane (including various isomers of tetramethylcyclohexane, such as 1,2,3,4-tetramethylcyclohexane, 1,2,4,5-tetramethylcyclohexane, 1,2,3,5-tetramethylcyclohexane), toluene, ethylbenzene and xylene (including o-xylene, m-xylene and p-xylene). The organic solvent is more preferably at least one selected from the group consisting of methylcyclohexane, heptane, cyclohexane, toluene, and xylene.

In the present invention, the amount of the organic solvent is not particularly limited, and may be conventionally selected. Generally, the organic solvent is used in an amount such that the concentration of the catalyst composition, in terms of the transition metal element in the transition metal compound, is 1-20 µmol/L. Specifically, the organic solvent is used in an amount such that the concentration of the catalyst composition, in terms of the transition metal element in the transition metal compound, is 1 µmol/L, 2 µmol/L, 3 µmol/L, 4 µmol/L, 5 µmol/L, 6 µmol/L, 7 µmol/L, 8 µmol/L, 9 µmol/L. L, 10 µmol/L, 11 µmol/L, 12 µmol/L, 13 µmol/L, 14 µmol/L, 15 µmol/L, 16 µmol/L, 17 µmol/L, 18 µmol/L, 19 µmol/L or 20 µmol/L. Preferably, the organic solvent is used in an amount such that the concentration of the catalyst composition, in terms of the transition metal element in the transition metal compound, is 5-10 µmol/L.

According to the ethylene oligomerization method of the present invention, the contacting may be carried out at a temperature of 0-200° C., for example: 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., 130° C., 131° C., 132°

C., 133° C., 134° C., 135° C., 136° C., 137° C., 138° C., 139° C., 140° C., 141° C., 142° C., 143° C., 144° C., 145° C., 146° C., 147° C., 148° C., 149° C., 150° C., 151° C., 152° C., 153° C., 154° C., 155° C., 156° C., 157° C., 158° C., 159° C., 160° C., 161° C., 162° C., 163° C., 164° C., 165° C., 166° C., 167° C., 168° C., 169° C., 170° C., 171° C., 172° C., 173° C., 174° C., 175° C., 176° C., 177° C., 178° C., 179° C., 180° C., 181° C., 182° C., 183° C., 184° C., 185° C., 186° C., 187° C., 188° C., 189° C., 190° C., 191° C., 192° C., 193° C., 194° C., 195° C., 196° C., 197° C., 198° C., 199° C. or 200° C.

Preferably, the contacting is carried out at a temperature of 0-100° C. More preferably, the contacting is carried out at a temperature of 30-90° C.

According to the ethylene oligomerization method of the present invention, the pressure of the ethylene may be 0.1-20 MPa, for example: 0.1 MPa, 0.2 MPa, 0.3 MPa, 0.4 MPa, 0.5 MPa, 0.6 MPa, 0.7 MPa, 0.8 MPa, 0.9 MPa, 1 MPa, 1.1 MPa, 1.2 MPa, 1.3 MPa, 1.4 MPa, 1.5 MPa, 1.6 MPa, 1.7 MPa, 1.8 MPa, 1.9 MPa, 2 MPa, 2.1 MPa, 2.2 MPa, 2.3 MPa, 2.4 MPa, 2.5 MPa, 2.6 MPa, 2.7 MPa, 2.8 MPa, 2.9 MPa, 3 MPa, 3.1 MPa, 3.2 MPa, 3.3 MPa, 3.4 MPa, 3.5 MPa, 3.6 MPa, 3.7 MPa, 3.8 MPa, 3.9 MPa, 4 MPa, 4.1 MPa, 4.2 MPa, 4.3 MPa, 4.4 MPa, 4.5 MPa, 4.6 MPa, 4.7 MPa, 4.8 MPa, 4.9 MPa, 5 MPa, 5.1 MPa, 5.2 MPa, 5.3 MPa, 5.4 MPa, 5.5 MPa, 5.6 MPa, 5.7 MPa, 5.8 MPa, 5.9 MPa, 6 MPa, 6.1 MPa, 6.2 MPa, 6.3 MPa, 6.4 MPa, 6.5 MPa, 6.6 MPa, 6.7 MPa, 6.8 MPa, 6.9 MPa, 7 MPa, 7.1 MPa, 7.2 MPa, 7.3 MPa, 7.4 MPa, 7.5 MPa, 7.6 MPa, 7.7 MPa, 7.8 MPa, 7.9 MPa, 8 MPa, 8.1 MPa, 8.2 MPa, 8.3 MPa, 8.4 MPa, 8.5 MPa, 8.6 MPa, 8.7 MPa, 8.8 MPa, 8.9 MPa, 9 MPa, 9.1 MPa, 9.2 MPa, 9.3 MPa, 9.4 MPa, 9.5 MPa, 9.6 MPa, 9.7 MPa, 9.8 MPa, 9.9 MPa, 10 MPa, 10.1 MPa, 10.2 MPa, 10.3 MPa, 10.4 MPa, 10.5 MPa, 10.6 MPa, 10.7 MPa, 10.8 MPa, 10.9 MPa, 11 MPa, 11.1 MPa, 11.2 MPa, 11.3 MPa, 11.4 MPa, 11.5 MPa, 11.6 MPa, 11.7 MPa, 11.8 MPa, 11.9 MPa, 12 MPa, 12.1 MPa, 12.2 MPa, 12.3 MPa, 12.4 MPa, 12.5 MPa, 12.6 MPa, 12.7 MPa, 12.8 MPa, 12.9 MPa, 13 MPa, 13.1 MPa, 13.2 MPa, 13.3 MPa, 13.4 MPa, 13.5 MPa, 13.6 MPa, 13.7 MPa, 13.8 MPa, 13.9 MPa, 14 MPa, 14.1 MPa, 14.2 MPa, 14.3 MPa, 14.4 MPa, 14.5 MPa, 14.6 MPa, 14.7 MPa, 14.8 MPa, 14.9 MPa, 15 MPa, 15.1 MPa, 15.2 MPa, 15.3 MPa, 15.4 MPa, 15.5 MPa, 15.6 MPa, 15.7 MPa, 15.8 MPa, 15.9 MPa, 16 MPa, 16.1 MPa, 16.2 MPa, 16.3 MPa, 16.4 MPa, 16.5 MPa, 16.6 MPa, 16.7 MPa, 16.8 MPa, 16.9 MPa, 17 MPa, 17.1 MPa, 17.2 MPa, 17.3 MPa, 17.4 MPa, 17.5 MPa, 17.6 MPa, 17.7 MPa, 17.8 MPa, 17.9 MPa, 18 MPa, 18.1 MPa, 18.2 MPa, 18.3 MPa, 18.4 MPa, 18.5 MPa, 18.6 MPa, 18.7 MPa, 18.8 MPa, 18.9 MPa, 19 MPa, 19.1 MPa, 19.2 MPa, 19.3 MPa, 19.4 MPa, 19.5 MPa, 19.6 MPa, 19.7 MPa, 19.8 MPa, 19.9 MPa or 20 MPa.

Preferably, the pressure of the ethylene is 0.5-10 MPa. More preferably, the pressure of the ethylene is 2-8 MPa.

According to the ethylene oligomerization method of the present invention, it may be performed by using a conventional method. In one embodiment, the halogen-containing compound, the transition metal compound, and the co-catalyst may be mixed, and then the mixture is added to a reactor, and is in contact with ethylene in the presence of an optional organic solvent to be subjected to an oligomerization reaction. In another embodiment, the halogen-containing compound, the transition metal compound, and the co-catalyst may be added to a reactor respectively, and be in contact with ethylene in the presence of an optional organic solvent to be subjected to an oligomerization reaction.

According to a fifth aspect, the present invention provides an ethylene trimerization method. The method includes a step of contacting ethylene with the catalyst composition according to the third aspect of the present invention at a temperature of 60° C. or above. In the present invention, "ethylene trimerization" means that the product formed by the ethylene trimerization is mainly C6 olefin (i.e., hexene), and the content of the C6 olefin may be 50% by weight or more, preferably 60% by weight or more.

According to the ethylene trimerization method of the present invention, the temperature for the contacting is preferably 60-90° C., for example 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C. or 90° C.

According to the ethylene trimerization method of the present invention, the contacting is preferably carried out in at least one organic solvent. The organic solvent is a solvent capable of dissolving an oligomerization product, and may be at least one selected from the group consisting of an alkane, a cycloalkane and an aromatic hydrocarbon, preferably at least one selected from the group consisting of $C_6$-$C_{12}$ alkane, $C_6$-$C_{12}$ cycloalkane, and $C_6$-$C_{12}$ aromatic hydrocarbon. Specific examples of the organic solvent may include, but are not limited to: hexane, 2-methylpentane, 3-methylpentane, 2,3-dimethylbutane, cyclohexane, methylcyclopentane, heptane, 2-methylhexane, 3-methylhexane, methylcyclohexane, 2-ethylpentane, 3-ethylpentane, 2,3-dimethylpentane, 2,4-dimethylpentane, octane, 2-methylheptane, 3-methylheptane, 4-methylheptane, 2,3-dimethylhexane, 2,4-dimethylhexane, 2,5-dimethylhexane, 3-ethylhexane, 2,2,3-trim ethylpentane, 2,3,3-trim ethylpentane, 2,4,4-trimethylpentane, 2-methyl-3-ethylpentane, nonane, 2-methyloctane, 3-methyloctane, 4-methyloctane, 2,3-dimethylheptane, 2,4-dimethylheptane, 3-ethylheptane, 4-ethylheptane, 2,3,4-trimethylhexane, 2,3,5-trimethylhexane, 2,4,5-trimethylhexane, 2,2,3-trimethylhexane, 2,2,4-trimethylhexane, 2,2,5-trimethylhexane, 2,3,3-trimethylhexane, 2,4,4-trimethylhexane, 2-methyl-3-ethylhexane, 2-methyl-4-ethylhexane, 3-methyl-3-ethylhexane, 3-methyl-4-ethylhexane, 3,3-diethylpentane, 1-methyl-2-ethylcyclohexane, 1-methyl-3-ethylcyclohexane, 1-methyl-4-ethylcyclohexane, n-propylcyclohexane, isopropylcyclohexane, trimethylcyclohexane (including various isomers of trim ethylcyclohexane, such as 1,2,3-trim ethylcyclohexane, 1,2,4-trim ethylcyclohexane, 1,2,5-trimethylcyclohexane, 1,3,5-trimethylcyclohexane), decane, 2-methylnonane, 3-methylnonane, 4-methylnonane, 5-methyl nonane, 2,3-dimethyloctane, 2,4-dimethyloctane, 3-ethyloctane, 4-ethyloctane, 2,3,4-trimethylheptane, 2,3,5-trimethylheptane, 2,3,6-trimethylheptane, 2,4,5-trimethylheptane, 2,4,6-trimethylheptane, 2,2,3-trimethylheptane, 2,2,4-trimethylheptane, 2,2,5-trimethylheptane, 2,2,6-trimethylheptane, 2,3,3-trimethylheptane, 2,4,4-trimethylheptane, 2-methyl-3-ethylheptane, 2-methyl-4-ethylheptane, 2-methyl-5-ethylheptane, 3-methyl-3-ethylheptane, 4-methyl-3-ethylheptane, 5-methyl-3-ethylheptane, 4-methyl-4-ethylheptane, 4-propylheptane, 3,3-diethylhexane, 3,4-diethylhexane, 2-methyl-3,3-diethylpentane, 1,2-diethylcyclohexane, 1,3-diethylcyclohexane, 1,4-diethylcyclohexane, n-butylcyclohexane, isobutylcyclohexane, tert-butyl cycl ° hexane, tetramethylcyclohexane (including various isomers of tetramethylcyclohexane, such as 1,2,3,4-tetramethylcyclohexane, 1,2,4,5-tetramethylcyclohexane, 1,2,3,5-tetramethylcyclohexane), toluene, ethylbenzene and xylene (including o-xylene, m-xylene and p-xylene). The organic solvent is more preferably at least one selected from the group consisting of methylcyclohexane, heptane, cyclohexane, toluene, and xylene.

In the present invention, the amount of the organic solvent is not particularly limited, and may be conventionally selected. Generally, the organic solvent is used in an amount such that the concentration of the catalyst composition, in terms of the transition metal element in the transition metal compound, is 1-20 µmol/L. Specifically, the organic solvent is used in an amount such that the concentration of the catalyst composition, in terms of the transition metal element in the transition metal compound, is 1 µmol/L, 2 µmol/L, 3 µmol/L, 4 µmol/L, 5 µmol/L, 6 µmol/L, 7 µmol/L, 8 µmol/L, 9 µmol/L, 10 µmol/L, 11 µmol/L, 12 µmol/L, 13 µmol/L, 14 µmol/L, 15 µmol/L, 16 µmol/L, 17 µmol/L, 18 µmol/L, 19 µmol/L or 20 µmol/L. Preferably, the organic solvent is used in an amount such that the concentration of the catalyst composition, in terms of the transition metal element in the transition metal compound, is 5-10 µmol/L.

According to the ethylene trimerization method of the present invention, the pressure of the ethylene may be 0.1-20 MPa, for example: 0.1 MPa, 0.2 MPa, 0.3 MPa, 0.4 MPa, 0.5 MPa, 0.6 MPa, 0.7 MPa, 0.8 MPa, 0.9 MPa, 1 MPa, 1.1 MPa, 1.2 MPa, 1.3 MPa, 1.4 MPa, 1.5 MPa, 1.6 MPa, 1.7 MPa, 1.8 MPa, 1.9 MPa, 2 MPa, 2.1 MPa, 2.2 MPa, 2.3 MPa, 2.4 MPa, 2.5 MPa, 2.6 MPa, 2.7 MPa, 2.8 MPa, 2.9 MPa, 3 MPa, 3.1 MPa, 3.2 MPa, 3.3 MPa, 3.4 MPa, 3.5 MPa, 3.6 MPa, 3.7 MPa, 3.8 MPa, 3.9 MPa, 4 MPa, 4.1 MPa, 4.2 MPa, 4.3 MPa, 4.4 MPa, 4.5 MPa, 4.6 MPa, 4.7 MPa, 4.8 MPa, 4.9 MPa, 5 MPa, 5.1 MPa, 5.2 MPa, 5.3 MPa, 5.4 MPa, 5.5 MPa, 5.6 MPa, 5.7 MPa, 5.8 MPa, 5.9 MPa, 6 MPa, 6.1 MPa, 6.2 MPa, 6.3 MPa, 6.4 MPa, 6.5 MPa, 6.6 MPa, 6.7 MPa, 6.8 MPa, 6.9 MPa, 7 MPa, 7.1 MPa, 7.2 MPa, 7.3 MPa, 7.4 MPa, 7.5 MPa, 7.6 MPa, 7.7 MPa, 7.8 MPa, 7.9 MPa, 8 MPa, 8.1 MPa, 8.2 MPa, 8.3 MPa, 8.4 MPa, 8.5 MPa, 8.6 MPa, 8.7 MPa, 8.8 MPa, 8.9 MPa, 9 MPa, 9.1 MPa, 9.2 MPa, 9.3 MPa, 9.4 MPa, 9.5 MPa, 9.6 MPa, 9.7 MPa, 9.8 MPa, 9.9 MPa, 10 MPa, 10.1 MPa, 10.2 MPa, 10.3 MPa, 10.4 MPa, 10.5 MPa, 10.6 MPa, 10.7 MPa, 10.8 MPa, 10.9 MPa, 11 MPa, 11.1 MPa, 11.2 MPa, 11.3 MPa, 11.4 MPa, 11.5 MPa, 11.6 MPa, 11.7 MPa, 11.8 MPa, 11.9 MPa, 12 MPa, 12.1 MPa, 12.2 MPa, 12.3 MPa, 12.4 MPa, 12.5 MPa, 12.6 MPa, 12.7 MPa, 12.8 MPa, 12.9 MPa, 13 MPa, 13.1 MPa, 13.2 MPa, 13.3 MPa, 13.4 MPa, 13.5 MPa, 13.6 MPa, 13.7 MPa, 13.8 MPa, 13.9 MPa, 14 MPa, 14.1 MPa, 14.2 MPa, 14.3 MPa, 14.4 MPa, 14.5 MPa, 14.6 MPa, 14.7 MPa, 14.8 MPa, 14.9 MPa, 15 MPa, 15.1 MPa, 15.2 MPa, 15.3 MPa, 15.4 MPa, 15.5 MPa, 15.6 MPa, 15.7 MPa, 15.8 MPa, 15.9 MPa, 16 MPa, 16.1 MPa, 16.2 MPa, 16.3 MPa, 16.4 MPa, 16.5 MPa, 16.6 MPa, 16.7 MPa, 16.8 MPa, 16.9 MPa, 17 MPa, 17.1 MPa, 17.2 MPa, 17.3 MPa, 17.4 MPa, 17.5 MPa, 17.6 MPa, 17.7 MPa, 17.8 MPa, 17.9 MPa, 18 MPa, 18.1 MPa, 18.2 MPa, 18.3 MPa, 18.4 MPa, 18.5 MPa, 18.6 MPa, 18.7 MPa, 18.8 MPa, 18.9 MPa, 19 MPa, 19.1 MPa, 19.2 MPa, 19.3 MPa, 19.4 MPa, 19.5 MPa, 19.6 MPa, 19.7 MPa, 19.8 MPa, 19.9 MPa or 20 MPa.

Preferably, the pressure of the ethylene is 0.5-5 MPa. More preferably, the pressure of the ethylene is 1~4 MPa. Further preferably, the pressure of the ethylene is 2-3 MPa.

According to the ethylene trimerization method of the present invention, it may be performed by using a conventional method. In one embodiment, the halogen-containing compound, the transition metal compound, and the co-catalyst may be mixed, and then the mixture is added to a reactor, and is in contact with ethylene in the presence of an optional organic solvent to be subjected to an oligomerization reaction. In another embodiment, the halogen-containing compound, the transition metal compound, and the co-catalyst may be added to a reactor respectively, and be in contact with ethylene in the presence of an optional organic solvent to be subjected to an oligomerization reaction.

According to a sixth aspect, the present invention provides an ethylene tetramerization method. The method includes a step of contacting ethylene with the catalyst composition according to the third aspect of the present invention at a temperature of lower than 60° C. In the present invention, "ethylene tetramerization" means that the product formed by the ethylene tetramerization reaction is mainly C8 olefin (i.e., octene), and the content of the C8 olefin may be 50% by weight or more, preferably 55% by weight or more.

According to the ethylene tetramerization method of the present invention, the temperature for the contacting is preferably 30-50° C., and may be, for example, 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C.

According to the ethylene tetramerization method of the present invention, the contacting is preferably carried out in at least one organic solvent. The organic solvent is a solvent capable of dissolving a tetramerization product, and may be at least one selected from the group consisting of an alkane, a cycloalkane and an aromatic hydrocarbon, preferably at least one selected from the group consisting of $C_6$-$C_{12}$ alkane, $C_6$-$C_{12}$ cycloalkane, and $C_6$-$C_{12}$ aromatic hydrocarbon. Specific examples of the organic solvent may include, but are not limited to: hexane, 2-methylpentane, 3-methylpentane, 2,3-dimethylbutane, cyclohexane, methylcyclopentane, heptane, 2-methylhexane, 3-methylhexane, methylcyclohexane, 2-ethylpentane, 3-ethylpentane, 2,3-dimethylpentane, 2,4-dimethylpentane, octane, 2-methylheptane, 3-methylheptane, 4-methylheptane, 2,3-dimethylhexane, 2,4-dimethylhexane, 2,5-dimethylhexane, 3-ethylhexane, 2,2,3-trimethylpentane, 2,3,3-trimethylpentane, 2,4,4-trimethylpentane, 2-methyl-3-ethylpentane, nonane, 2-methyloctane, 3-methyloctane, 4-methyloctane, 2,3-dimethylheptane, 2,4-dimethylheptane, 3-ethylheptane, 4-ethylheptane, 2,3,4-trimethylhexane, 2,3,5-trimethylhexane, 2,4,5-trimethylhexane, 2,2,3-trimethylhexane, 2,2,4-trimethylhexane, 2,2,5-trimethylhexane, 2,3,3-trimethylhexane, 2,4,4-trimethylhexane, 2-methyl-3-ethylhexane, 2-methyl-4-ethylhexane, 3-methyl-3-ethyl hexan e, 3-methyl-4-ethylhexane, 3,3-diethylpentane, 1-methyl-2-ethylcyclohexane, 1-methyl-3-ethylcyclohexane, 1-methyl-4-ethylcyclohexane, n-propylcyclohexane, isopropylcyclohexane, trimethylcyclohexane (including various isomers of trimethylcyclohexane, such as 1,2,3-trimethylcyclohexane, 1,2,4-trimethylcyclohexane, 1,2,5-trimethylcyclohexane, 1,3,5-trimethylcyclohexane), decane, 2-methylnonane, 3-methylnonane, 4-methylnonane, 5-methylnonane, 2,3-dimethyloctane, 2,4-dimethyloctane, 3-ethyloctane, 4-ethyloctane, 2,3,4-trimethylheptane, 2,3,5-trimethylheptane, 2,3,6-trimethylheptane, 2,4,5-trimethylheptane, 2,4,6-trimethylheptane, 2,2,3-trimethylheptane, 2,2,4-trimethylheptane, 2,2,5-trimethylheptane, 2,2,6-trimethylheptane, 2,3,3-trimethylheptane, 2,4,4-trimethylheptane, 2-methyl-3-ethylheptane, 2-methyl-4-ethylheptane, 2-methyl-5-ethylheptane, 3-methyl-3-ethylheptane, 4-methyl-3-ethylheptane, 5-methyl-3-ethylheptane, 4-methyl-4-ethylheptane, 4-propylheptane, 3,3-diethylhexane, 3,4-diethylhexane, 2-methyl-3,3-diethylpentane, 1,2-di ethylcyclohexane, 1,3-diethylcyclohexane, 1,4-diethylcyclohexane, n-butylcyclohexane, isobutylcyclohexane, tert-butylcyclohexane, tetramethylcyclohexane (including various isomers of tetramethylcyclohexane, such as 1,2,3,4-tetramethylcyclohexane, 1,2,4,5-tetramethylcyclohexane, 1,2,3,5-tetramethylcyclohexane), toluene, ethylbenzene and xylene (including o-xylene, m-xylene and p-xylene). The organic solvent is more preferably at least one selected from the group consisting of methylcyclohexane, heptane, cyclohexane, toluene, and xylene.

In the present invention, the amount of the organic solvent is not particularly limited, and may be conventionally selected. Generally, the organic solvent is used in an amount such that the concentration of the catalyst composition, in terms of the transition metal element in the transition metal compound, is 1-20 μmol/L. Specifically, the organic solvent is used in an amount such that the concentration of the catalyst composition, in terms of the transition metal element in the transition metal compound, is 1 μmol/L, 2 μmol/L, 3 μmol/L, 4 μmol/L, 5 μmol/L, 6 μmol/L, 7 μmol/L, 8 μmol/L, 9 μmol/L, 10 μmol/L, 11 μmol/L, 12 μmol/L, 13 μmol/L, 14 μmol/L, 15 μmol/L, 16 μmol/L, 17 μmol/L, 18 μmol/L, 19 μmol/L or 20 μmol/L. Preferably, the organic solvent is used in an amount such that the concentration of the catalyst composition, in terms of the transition metal element in the transition metal compound, is 5-10 μmol/L.

According to the ethylene tetramerization method of the present invention, the pressure of the ethylene may be 0.1-20 MPa, for example: 0.1 MPa, 0.2 MPa, 0.3 MPa, 0.4 MPa, 0.5 MPa, 0.6 MPa, 0.7 MPa, 0.8 MPa, 0.9 MPa, 1 MPa, 1.1 MPa, 1.2 MPa, 1.3 MPa, 1.4 MPa, 1.5 MPa, 1.6 MPa, 1.7 MPa, 1.8 MPa, 1.9 MPa, 2 MPa, 2.1 MPa, 2.2 MPa, 2.3 MPa, 2.4 MPa, 2.5 MPa, 2.6 MPa, 2.7 MPa, 2.8 MPa, 2.9 MPa, 3 MPa, 3.1 MPa, 3.2 MPa, 3.3 MPa, 3.4 MPa, 3.5 MPa, 3.6 MPa, 3.7 MPa, 3.8 MPa, 3.9 MPa, 4 MPa, 4.1 MPa, 4.2 MPa, 4.3 MPa, 4.4 MPa, 4.5 MPa, 4.6 MPa, 4.7 MPa, 4.8 MPa, 4.9 MPa, 5 MPa, 5.1 MPa, 5.2 MPa, 5.3 MPa, 5.4 MPa, 5.5 MPa, 5.6 MPa, 5.7 MPa, 5.8 MPa, 5.9 MPa, 6 MPa, 6.1 MPa, 6.2 MPa, 6.3 MPa, 6.4 MPa, 6.5 MPa, 6.6 MPa, 6.7 MPa, 6.8 MPa, 6.9 MPa, 7 MPa, 7.1 MPa, 7.2 MPa, 7.3 MPa, 7.4 MPa, 7.5 MPa, 7.6 MPa, 7.7 MPa, 7.8 MPa, 7.9 MPa, 8 MPa, 8.1 MPa, 8.2 MPa, 8.3 MPa, 8.4 MPa, 8.5 MPa, 8.6 MPa, 8.7 MPa, 8.8 MPa, 8.9 MPa, 9 MPa, 9.1 MPa, 9.2 MPa, 9.3 MPa, 9.4 MPa, 9.5 MPa, 9.6 MPa, 9.7 MPa, 9.8 MPa, 9.9 MPa, 10 MPa, 10.1 MPa, 10.2 MPa, 10.3 MPa, 10.4 MPa, 10.5 MPa, 10.6 MPa, 10.7 MPa, 10.8 MPa, 10.9 MPa, 11 MPa, 11.1 MPa, 11.2 MPa, 11.3 MPa, 11.4 MPa, 11.5 MPa, 11.6 MPa, 11.7 MPa, 11.8 MPa, 11.9 MPa, 12 MPa, 12.1 MPa, 12.2 MPa, 12.3 MPa, 12.4 MPa, 12.5 MPa, 12.6 MPa, 12.7 MPa, 12.8 MPa, 12.9 MPa, 13 MPa, 13.1 MPa, 13.2 MPa, 13.3 MPa, 13.4 MPa, 13.5 MPa, 13.6 MPa, 13.7 MPa, 13.8 MPa, 13.9 MPa, 14 MPa, 14.1 MPa, 14.2 MPa, 14.3 MPa, 14.4 MPa, 14.5 MPa, 14.6 MPa, 14.7 MPa, 14.8 MPa, 14.9 MPa, 15 MPa, 15.1 MPa, 15.2 MPa, 15.3 MPa, 15.4 MPa, 15.5 MPa, 15.6 MPa, 15.7 MPa, 15.8 MPa, 15.9 MPa, 16 MPa, 16.1 MPa, 16.2 MPa, 16.3 MPa, 16.4 MPa, 16.5 MPa, 16.6 MPa, 16.7 MPa, 16.8 MPa, 16.9 MPa, 17 MPa, 17.1 MPa, 17.2 MPa, 17.3 MPa, 17.4 MPa, 17.5 MPa, 17.6 MPa, 17.7 MPa, 17.8 MPa, 17.9 MPa, 18 MPa, 18.1 MPa, 18.2 MPa, 18.3 MPa, 18.4 MPa, 18.5 MPa, 18.6 MPa, 18.7 MPa, 18.8 MPa, 18.9 MPa, 19 MPa, 19.1 MPa, 19.2 MPa, 19.3 MPa, 19.4 MPa, 19.5 MPa, 19.6 MPa, 19.7 MPa, 19.8 MPa, 19.9 MPa or 20 MPa.

Preferably, the pressure of the ethylene is 0.5-8 MPa. More preferably, the pressure of the ethylene is 3-6 MPa. Further preferably, the pressure of the ethylene is 4-5 MPa.

According to the ethylene tetramerization method of the present invention, it may be performed by using a conventional method. In one embodiment, the halogen-containing compound, the transition metal compound, and the co-catalyst may be mixed, and then the mixture is added to a reactor, and is in contact with ethylene in the presence of an optional organic solvent to be subjected to an oligomerization reaction. In another embodiment, the halogen-containing compound, the transition metal compound, and the co-catalyst may be added to a reactor respectively, and be in contact with ethylene in the presence of an optional organic solvent to be subjected to an oligomerization reaction.

The present invention will be illustrated in detail below in connection with the examples, not thereby limiting the scope of the invention.

In the following examples and comparative examples, the nuclear magnetic resonance spectroscopy analysis was performed by using Bruker AV400 nuclear magnetic resonance spectrometer, wherein the detection condition for nuclear magnetic resonance were: deuterated chloroform was used as a solvent and a test was performed at room temperature.

In the following examples and comparative examples, the gas chromatographic analysis was performed by HP 5890 chromatograph, wherein the detection condition for the gas chromatograph were: a chromatographic column was an SE-54 chromatographic column, high-purity nitrogen was used as a carrier gas and a FID detector was used; the temperature of the column was increased by a two-step procedure, specifically: the initial temperature was 40° C., keeping for 5 minutes, then the temperature was raised to 300° C. at 30° C./min, keeping for 15 minutes.

In the following examples and comparative examples, the catalyst activity was indicated as the mass of a polymerization product generated with a unit mass of catalyst during the unit polymerization time, wherein the catalyst was measured in terms of the metal element in the transition metal compound (in terms of moles), the polymerization time was measured in hours, and the polymerization product was measured in grams.

In the following examples and comparative examples, selectivity=(the mass of the target product in the polymerization reaction product/the total mass of the polymerization reaction product)×100%.

The meanings of the abbreviations involved in the following examples and comparative examples are as follows:

$^t$Bu is tert-butyl; $^i$Pr is isopropyl; Cy is cyclohexyl; Ph is phenyl; Et is ethyl; THF is tetrahydrofuran; acac is acetylacetone; and Me is methyl.

Preparation examples 1-12 are used to prepare halogen-containing compounds according to the present invention.

Preparation Example 1

Preparation example 1 was used to prepare a halogen-containing compound $I^1$.

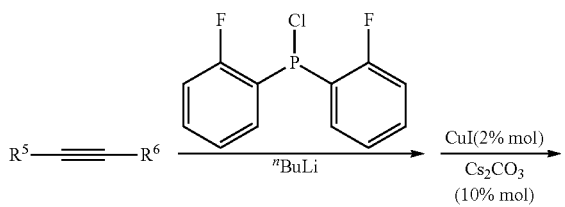

17
-continued

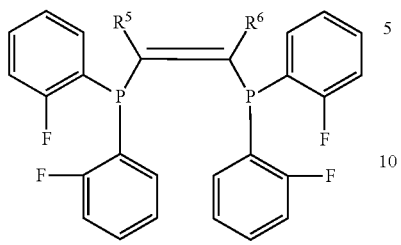

The halogen-containing compound I¹ may be prepared with reference to the above reaction formula, with specific steps as follows:

Under the protection of nitrogen, n-butyllithium (11 mmol) (6.6 mL of n-butyllithium in hexane, the concentration of n-butyllithium being 1.6 M) was added into a reaction flask containing 15 mL of dry tetrahydrofuran, the mixture was cooled down to 0° C., 2.2 g (10 mmol) of difluorophenylphosphonium chloride was added under stirring, then acetylene (11 mmol) was added, stirring was continued to be performed for 0.5 h, then the temperature was raised to room temperature (25° C., the same below), and stirring was continued to be performed for 2 h. A catalytic amount of CuI and cesium carbonate were added, then 2.2 g (10 mmol) of difluorophenylphosphonium chloride was added, the temperature was raised to 90° C., and stirring was performed for 4 h at 90° C. After the reaction was completed, the reaction mixture was cooled to room temperature and filtered. The filtrate was drained under reduced pressure, and the resulting residue was allowed to pass through a silica gel column (petroleum ether (PE)/ethyl acetate (EA)=20:1) to obtain the halogen-containing compound I¹.

The prepared compound was subjected to nuclear magnetic resonance analysis, and it may be demonstrated that the prepared compound was the halogen-containing compound represented by the formula I, wherein all of $R^1$, $R^2$, $R^3$ and $R^4$ are fluorine and ortho-substituents, and $R^5$ and $R^6$ are hydrogen.

H¹ NMR (400 MHz, CDCl₃): δ=7.30-7.00 (m, 16H), 5.06 (s, 2H).

Preparation Example 2

Preparation example 2 was used to prepare a halogen-containing compound I².

In this preparation example, the halogen-containing compound was prepared by the same method as the preparation example 1, except that the difluorophenylphosphonium chloride was replaced with dichlorophenylphosphonium chloride. The prepared compound was subjected to nuclear magnetic resonance analysis, and it may be determined that the prepared compound was the compound represented by the formula I, wherein all of $R^1$, $R^2$, $R^3$ and $R^4$ are chlorine and ortho-substituents, and $R^5$ and $R^6$ are hydrogen.

H¹NMR (400 MHz, CDCl₃): δ=7.30-7.00 (m, 16H), 5.18 (s, 2H).

Preparation Example 3

Preparation example 3 was used to prepare a halogen-containing compound I³.

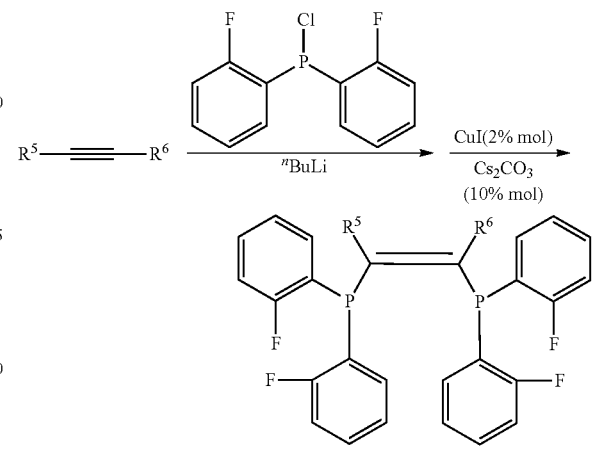

The halogen-containing compound I³ may be prepared with reference to the above reaction formula, with specific steps as follows:

Tert-butyl acetylene (11 mmol) and 15 mL of dry tetrahydrofuran were added to a 50 mL reaction flask under the protection of nitrogen, and then n-butyl lithium (11 mmol) (6.6 mL n-butyl lithium in hexane, the concentration of n-butyl lithium being 1.6M) was added dropwise at 0° C. After the addition dropwise was completed, the mixture was continued to be stirred at 0° C. for 30 min, and subsequently 2.2 g (10 mmol) of difluorophenylphosphonium chloride was added dropwise. After the addition dropwise was completed, the temperature was raised to room temperature (25° C., the same below), and stirring was continued to be performed for 2 h. A catalytic amount of CuI and cesium carbonate were added, then 2.2 g (10 mmol) of difluorophenylphosphonium chloride was added, the temperature was raised to 90° C., and stirring was performed for 4 h at 90° C. After the reaction was completed, the reaction mixture was cooled to room temperature and filtered. The filtrate was drained under reduced pressure, and the resulting residue was allowed to pass through a silica gel column (petroleum ether (PE)/ethyl acetate (EA)=20:1) to obtain the halogen-containing compound I³. The prepared compound was subjected to nuclear magnetic resonance analysis, and it may be determined that the prepared compound was the halogen-containing compound represented by the formula I, wherein all of $R^1$, $R^2$, $R^3$ and $R^4$ are fluorine and ortho-substituents, $R^5$ is ᵗBu, and $R^6$ is hydrogen. H¹ NMR (400 MHz, CDCl₃): δ=7.27-7.00 (m, 16H), 4.95 (s, 1H), 1.16 (s, 9H).

Preparation Example 4

Preparation example 4 was used to prepare a halogen-containing compound I⁴.

In this preparation example, the halogen-containing compound was prepared by the same method as the preparation example 3, except that the tert-butyl acetylene was replaced with isopropyl acetylene. The prepared compound was subjected to nuclear magnetic resonance analysis, and it may be determined that the prepared compound was the halogen-containing compound represented by the formula I, wherein all of $R^1$, $R^2$, $R^3$ and $R^4$ are fluorine and ortho-substituents, and $R^5$ is $^i$Pr, $R^6$ is hydrogen.

$H^1$ NMR (400 MHz, CDCl$_3$): δ=7.29-7.00 (m, 16H), 4.96 (s, 1H), 2.50 (m, 1H), 1.12 (d, 6H).

Preparation Example 5

Preparation example 5 was used to prepare a halogen-containing compound $I^5$.

In this preparation example, the halogen-containing compound was prepared by the same method as the preparation example 3, except that the tert-butyl acetylene was replaced with cyclohexylacetylene. The prepared compound was subjected to nuclear magnetic resonance analysis, and it may be determined that the prepared compound was the halogen-containing compound represented by the formula I, wherein all of $R^1$, $R^2$, $R^3$ and $R^4$ are fluorine and ortho-substituents, $R^5$ is Cy, $R^6$ is hydrogen.

NMR (400 MHz, CDCl$_3$): δ=7.29-6.98 (m, 16H), 4.89 (s, 1H), 2.10 (m, 1H), 1.30-1.60 (m, 10H).

Preparation Example 6

Preparation example 6 was used to prepare a halogen-containing compound $I^6$.

In this preparation example, the halogen-containing compound was prepared by the same method as the preparation example 3, except that the tert-butyl acetylene was replaced with phenylacetylene. The prepared compound was subjected to nuclear magnetic resonance analysis, and it may be determined that the prepared compound was the compound represented by the formula I, wherein all of $R^1$, $R^2$, $R^3$ and $R^4$ are fluorine and ortho-substituents, and $R^5$ is Ph, $R^6$ is hydrogen.

NMR (400 MHz, CDCl$_3$): δ=7.35-7.00 (m, 21H), 5.55 (s, 1H).

Preparation Example 7

Preparation example 7 was used to prepare a halogen-containing compound $I^7$.

In this preparation example, the halogen-containing compound was prepared by the same method as the preparation example 3, except that the tert-butyl acetylene was replaced with allylene. The prepared compound was subjected to nuclear magnetic resonance analysis, and it may be determined that the prepared compound was the compound represented by the formula I, wherein all of $R^1$, $R^2$, $R^3$ and $R^4$ are fluorine and ortho-substituents, and $R^5$ is Me, $R^6$ is hydrogen.

$H^1$ NMR (400 MHz, CDCl$_3$,): δ=7.29-6.99 (m, 16H), 4.97 (s, 1H), 1.68 (s, 3H).

Preparation Example 8

Preparation example 8 was used to prepare a halogen-containing compound $I^8$.

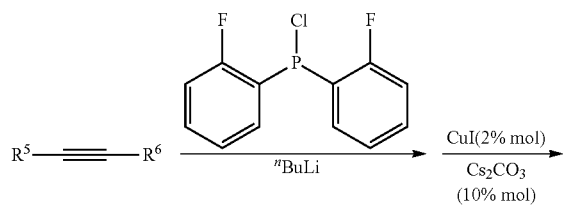

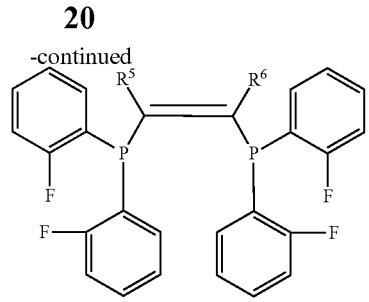

The halogen-containing compound $I^8$ may be prepared with reference to the above reaction formula, with specific steps as follows:

2-Butyne (11 mmol) and 15 mL of dry tetrahydrofuran were added to a 50 mL reaction flask under the protection of nitrogen, and then n-butyllithium (11 mmol) (6.6 mL n-butyllithium in hexane, the concentration of n-butyllithium being 1.6M) was added dropwise at 0° C. After the addition dropwise was completed, the mixture was continued to be stirred at 0° C. for 30 min, and subsequently 2.2 g (10 mmol) of difluorophenylphosphonium chloride was added dropwise. After the addition dropwise was completed, the temperature was raised to room temperature (25° C., the same below), and stirring was continued to be performed for 2 h. A catalytic amount of CuI and cesium carbonate were added, then 2.2 g (10 mmol) of difluorophenylphosphonium chloride was added, the temperature was raised to 90° C. and stirring was performed for 4 h at 90° C. After the reaction was completed, the reaction mixture was cooled to room temperature and filtered. The filtrate was drained under reduced pressure, and the residue was allowed to pass through a silica gel column (petroleum ether (PE)/ethyl acetate (EA)=20:1) to obtain the halogen-containing compound $I^8$.

The prepared compound was subjected to nuclear magnetic resonance analysis, and it may be determined that the prepared compound was the halogen-containing compound represented by the formula I, wherein all of $R^1$, $R^2$, $R^3$ and $R^4$ are fluorine and ortho-substituents, and both $R^5$ and $R^6$ are Me.

$H^1$NMR (400 MHz, CDCl$_3$): δ=7.30-7.00 (m, 16H), 1.68 (s, 6H).

Preparation Example 9

Preparation example 9 was used to prepare a halogen-containing compound $I^9$.

In this preparation example, the halogen-containing compound was prepared by the same method as the preparation example 8, except that the 2-butyne was replaced with 2,5-dimethyl-3-hexyne. The prepared compound was subjected to nuclear magnetic resonance analysis, and it may be determined that the prepared compound was the halogen-containing compound represented by the formula I, wherein all of $R^1$, $R^2$, $R^3$ and $R^4$ are fluorine and ortho-substituents, and both $R^5$ and $R^6$ are $^i$Pr.

NMR (400 MHz, CDCl$_3$): δ=7.35-7.00 (m, 16H), 2.70 (m, 2H), 1.15-1.10 (m, 12H).

Preparation Example 10

Preparation example 10 was used to prepare a halogen-containing compound $I^{10}$.

In this preparation example, the halogen-containing compound was prepared by the same method as the preparation example 8, except that the 2-butyne was replaced with dicyclohexylacetylene. The prepared compound was subjected to nuclear magnetic resonance analysis, and it may be determined that the prepared compound was the halogen-containing compound represented by the formula I, wherein all of $R^1$, $R^2$, $R^3$ and $R^4$ are fluorine and ortho-substituents, and both $R^5$ and $R^6$ are Cy.

NMR (400 MHz, CDCl$_3$): δ=7.35-6.99 (m, 16H), 2.15 (m, 2H), 1.30-1.60 (m, 20H).

Preparation Example 11

Preparation example 11 was used to prepare a halogen-containing compound $I^{11}$.

In this preparation example, the halogen-containing compound was prepared by the same method as the preparation example 8, except that the 2-butyne was replaced with diphenylacetylene. The prepared compound was subjected to nuclear magnetic resonance analysis, and it may be determined that the prepared compound was the halogen-containing compound represented by the formula I, wherein all of $R^1$, $R^2$, $R^3$ and $R^4$ are fluorine and ortho-substituents, and both $R^5$ and $R^6$ are Ph.

$H^1$ NMR (400 MHz, CDCl$_3$): δ=7.45-7.00 (m, 26H).

Preparation Example 12

Preparation example 12 was used to prepare a halogen-containing compound $I^{12}$.

In this preparation example, the halogen-containing compound was prepared by the same method as the preparation example 8, except that the 2-butyne was replaced with 2,2,5,5-tetramethyl-3-hexyne. The prepared compound was subjected to nuclear magnetic resonance analysis, and it may be determined that the prepared compound was the halogen-containing compound represented by the formula I, wherein all of $R^1$, $R^2$, $R^3$ and $R^4$ are fluorine and ortho-substituents, and both $R^5$ and $R^6$ are $^t$Bu.

$H^1$ NMR (400 MHz, CDCl$_3$): δ=7.25-6.97 (m, 16H), 1.20 (s, 18H).

Examples 1-44 were used to illustrate the present invention.

Example 1

A 300 mL stainless steel polymerization autoclave was heated to 80° C., and vacuumized, then replacement was performed with nitrogen, and subsequently ethylene was charged for replacement. Then, the temperature in the autoclave was lowered to 40° C. Methylcyclohexane (purchased from J&K chemicals, Beijing), 0.5 μmol chromium acetylacetonate (purchased from J&K chemicals, Beijing), the halogen-containing compound $I^1$ (wherein, $R^1$, $R^2$, $R^3$ and $R^4$ are all fluorine and ortho-substituents, and both $R^5$ and $R^6$ are hydrogen) as a ligand, and modified methylaluminoxane (MMAO, purchased from Akzo Nobel) as a co-catalyst were added into the autoclave, and mixed evenly, wherein the total volume of the mixed solution was 100 mL, and the molar ratio of chromium acetylacetonate to the halogen-containing compound to the co-catalyst was 1:2:400, that is, the addition amount of the halogen-containing compound $I^1$ was and the addition amount of MMAO was 200 Ethylene was introduced, the pressure of ethylene was controlled to be 3 MPa, and ethylene oligomerization was carried out at a temperature of 40° C. After 30 minutes, 1 mL of ethanol was added as a terminator to terminate the reaction. The temperature in the autoclave was lowered to room temperature (25° C.), and the gas phase products were collected into a gas measuring tank, the liquid phase products were collected into an erlenmeyer flask. The gas and liquid products were measured respectively and analyzed by gas chromatography to calculate the catalyst activity and the product composition, and the results were listed in Table 1.

Example 2

The ethylene oligomerization was carried out by using the same method as Example 1, except that the halogen-containing compound as the ligand was replaced with the halogen-containing compound $I^2$ (wherein, $R^1$, $R^2$, $R^3$ and $R^4$ are all fluorine and ortho-substituents, and both $R^5$ and $R^6$ are hydrogen), and the experimental results were listed in Table 1.

Example 3

The ethylene oligomerization was carried out by using the same method as Example 1, except that the modified methylaluminoxane as the co-catalyst was replaced with triethylaluminum (purchased from J&K chemicals, Beijing). The experimental results were listed in Table 1.

Example 4

The ethylene oligomerization was carried out by using the same method as Example 1, except that chromium acetylacetonate was replaced with tris(tetrahydrofuran) chromium trichloride (purchased from J&K chemicals, Beijing). The experimental results were listed in Table 1.

Example 5

The ethylene oligomerization was carried out by using the same method as Example 1, except that the ethylene oligomerization was carried out at a temperature of 50° C. The experimental results were listed in Table 1.

Example 6

The ethylene oligomerization was carried out by using the same method as Example 1, except that the ethylene oligomerization was carried out at a temperature of 60° C. The experimental results were listed in Table 1.

Example 7

The ethylene oligomerization was carried out by using the same method as Example 1, except that the ethylene oligomerization was carried out at a temperature of 70° C. The experimental results were listed in Table 1.

Example 8

The ethylene oligomerization was carried out by using the same method as Example 1, except that the ethylene oligomerization was carried out at a temperature of 90° C. The experimental results were listed in Table 1.

Example 9

The ethylene oligomerization was carried out by using the same method as Example 1, except that the ethylene oligomerization was carried out at a temperature of 30° C. The experimental results were listed in Table 1.

Example 10

The ethylene oligomerization was carried out by using the same method as Example 1, except that the pressure of ethylene was controlled to be 5 MPa, and the experimental results were listed in Table 1.

Comparative Example 1

The ethylene oligomerization was carried out by using the same method as Example 1, except that the halogen-containing compound was replaced with (S,S)-(phenyl)$_2$PCH(Me)CH(Me)P(phenyl)$_2$ (marked as D1), and the experimental results were listed in Table 1.

Comparative Example 2

The ethylene oligomerization was carried out by using the same method as Example 1, except that the halogen-containing compound was replaced with (S,S)-(o-fluoro-phenyl)$_2$PCH(Me)CH(Me)P(o-fluoro-phenyl)$_2$ (marked as D2), and the experimental results were listed in Table 1.

Comparative Example 3

The ethylene oligomerization was carried out by using the same method as Example 1, except that the halogen-containing compound was replaced with

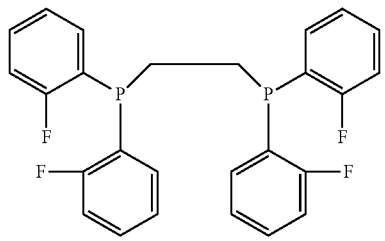 [SMILES: Fc1ccccc1P(CCP(c1ccccc1F)c1ccccc1F)c1ccccc1F]

(marked as D3), and the experimental results were listed in Table 1.

Comparative Example 4

The ethylene oligomerization was carried out by using the same method as Example 1, except that the halogen-containing compound was replaced with

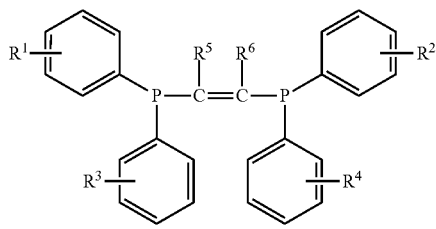

(marked as D4), wherein $R^2$, $R^3$, $R^4$ and $R^6$ are hydrogen, $R^1$ is fluorine (as an ortho-substituent), $R^5$ is tert-butyl, and the experimental results were listed in Table 1.

Comparative Example 5

The ethylene oligomerization was carried out by using the same method as Example 1, except that the halogen-containing compound was replaced by

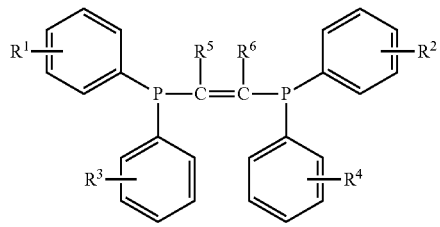

(marked as D5), wherein $R^2$, $R^3$, $R^4$ and $R^6$ are hydrogen, and $R^1$ is fluorine (as an ortho-substituent), and $R^5$ is methyl, and the experimental results were listed in Table 1.

Comparative Example 6

The ethylene oligomerization reaction was carried out by using the same method as Example 1, except that the halogen-containing compound was replaced by

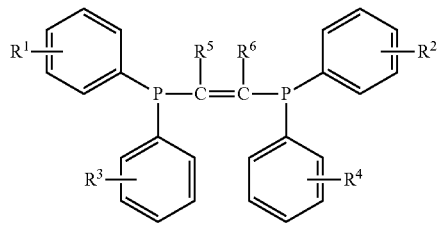

(marked as D6), wherein $R^2$, $R^3$, $R^4$ and $R^6$ are hydrogen, and $R^1$ is fluorine (as an ortho-substituent), and $R^5$ is cyclohexyl, and the experimental results are listed in Table 1.

Example 11

A 300 mL stainless steel polymerization autoclave was heated to 80° C., and vacuumized, then replacement was performed with nitrogen, and subsequently ethylene was charged for replacement. Then, the temperature in the autoclave was lowered to 50° C. Heptane (purchased from J&K chemicals, Beijing), 0.5 μmol chromium acetylacetonate (purchased from J&K chemicals, Beijing), the halogen-containing compound I$^i$ as a ligand (wherein, $R^1$, $R^2$, $R^3$ and $R^4$ are all fluorine and ortho-substituents, and both $R^5$ and $R^6$ are hydrogen), and modified methylaluminoxane (MMAO, purchased from Akzo Nobel) as a co-catalyst were added into the autoclave, and mixed uniformly, wherein the total volume of the mixed solution was 100 mL, and the molar ratio of chromium acetylacetonate to the halogen-containing compound to the co-catalyst is 1:2:500. That is, the addition amount of the halogen-containing compound I$^i$ was 1 and the addition amount of MMAO was 250 Ethylene was introduced, the pressure of ethylene was controlled to be 4 MPa, and ethylene oligomerization was carried out at a temperature of 50° C. After 60 minutes, 1 mL of ethanol was added as a terminator to terminate the reaction. The temperature in the autoclave was lowered to room temperature (25° C.). The gas phase products were collected in a gas measuring tank, and the liquid phase products were collected in an erlenmeyer flask, and the gas and liquid products were measured separately and analyzed by gas chromatography to calculate the catalyst activity and the product composition, and the results were listed in Table 1.

Example 12

A 300 mL stainless steel polymerization autoclave was heated to 80° C., and vacuumized, then replacement was performed with nitrogen, and subsequently ethylene was charged for replacement. Toluene (purchased from J&K chemicals, Beijing), 1.0 µmol chromium acetylacetonate (purchased from J&K chemicals, Beijing), the halogen-containing compound (wherein, $R^1$, $R^2$, $R^3$ and $R^4$ are all fluorine and ortho-substituents, and both $R^5$ and $R^6$ are hydrogen) as a ligand, and methylaluminoxane (MAO, purchased from Akzo Nobel) as a co-catalyst were added into the autoclave, and mixed uniformly, wherein the total volume of the mixed solution was 100 mL, and the molar ratio of chromium acetylacetonate to the halogen-containing compound to the co-catalyst was 1:1.5:300, that is, the addition amount of the halogen-containing compound $I^i$ is 1.5 and the addition amount of MAO is 300 Ethylene was introduced, the pressure of ethylene was controlled to be 2 MPa, and ethylene oligomerization was carried out at a temperature of 80° C. After 30 minutes, 1 mL of ethanol was added as a terminator to terminate the reaction. The temperature in the autoclave was lowered to room temperature (25° C.). The gas phase products were collected in a gas measuring tank, the liquid phase products were collected in an erlenmeyer flask, and the gas and liquid products were measured separately and analyzed by gas chromatography to calculate the catalyst activity and the product composition, and the results were listed in Table 1.

Comparative Example 7

The ethylene oligomerization was carried out by the same method as Example 12, except that the halogen-containing compound was replaced with (S,S)-(o-fluoro-phenyl)$_2$PCH(Me)CH(Me)P(o-fluoro-phenyl)$_2$ (marked as D2), and the experimental results were listed in Table 1.

Example 13

A 300 mL stainless steel polymerization autoclave was heated to 80° C., and vacuumized, then replacement was performed with nitrogen, and subsequently ethylene was charged for replacement. Then, methylcyclohexane (purchased from J&K chemicals, Beijing), 0.2 µmol tris(tetrahydrofuran)chromium trichloride (purchased from J&K chemicals, Beijing), the halogen-containing compound $I^1$ (wherein, $R^1$, $R^2$, $R^3$ and $R^4$ are all fluorine and ortho-substituents, and both $R^5$ and $R^6$ are hydrogen) as a ligand, and modified methylaluminoxane (MMAO, purchased from Akzo Nobel) as a co-catalyst were added into the autoclave, and mixed uniformly, wherein the total volume of the mixed solution was 100 mL, and the molar ratio of chromium acetylacetonate to the halogen-containing compound to the co-catalyst is 1:1:500. That is, the addition amount of the halogen-containing compound $I^i$ was 0.2 and the addition amount of MMAO was 100 Ethylene was introduced, the pressure of ethylene was controlled to be 3 MPa, and ethylene oligomerization was carried out at a temperature of 60° C. After 60 minutes, 2.0 mL of 2-ethyl hexanol was added as a terminator to terminate the reaction. The temperature in the autoclave was lowered to room temperature (25° C.). The gas phase products were collected in a gas measuring tank, and the liquid phase products were collected in an erlenmeyer flask, and the gas and liquid products were measured separately and analyzed by gas chromatography to calculate the catalyst activity and the product composition, and the results were listed in Table 1.

Example 14

The ethylene oligomerization was carried out by using the same method as Example 13, except that the ethylene oligomerization was carried out at a temperature of 100° C.

Comparative Example 8

The ethylene oligomerization was carried out by using the same method as Example 13, except that the halogen-containing compound was replaced with

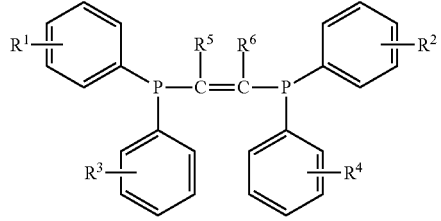

(marked as D7), wherein $R^2$, $R^3$, $R^4$ and $R^6$ are hydrogen, $R^1$ is an ortho-fluoro group, and $R^5$ is methyl, and the experimental results were listed in Table 1.

Comparative Example 9

The ethylene oligomerization was carried out by using the same method as Example 14, except that the halogen-containing compound was replaced with

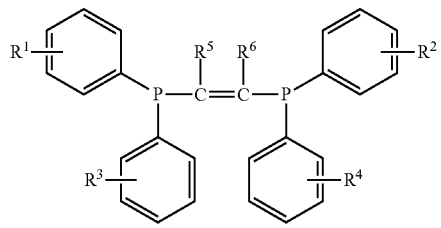

(marked as D8), wherein $R^3$, $R^4$ and $R^6$ are hydrogen, $R^1$ and $R^2$ are an ortho-fluoro group, respectively, $R^5$ is cyclohexyl, and the experimental results were listed in Table 1.

TABLE 1

| Groups | catalyst composition (molar ratio) | Activity $10^8 g \cdot mol(Cr)^{-1} \cdot h^{-1}$ | C6 Selectivity, wt % | Content of 1-hexene in C6, % | C8 Selectivity, wt % | Content of 1-octene in C8, % | Total selectivity of 1-hexene and 1-octene wt % |
|---|---|---|---|---|---|---|---|
| Example 1 | $I^1$/Cr(acac)$_3$/MMAO = 2/1/400 | 2.08 | 35.8 | 95.4 | 61.2 | 99.6 | 95.1 |
| Example 2 | $I^1$/Cr(acac)$_3$/MMAO = 2/1/400 | 0.78 | 45.0 | 90.1 | 50.3 | 99.4 | 90.5 |
| Example 3 | $I^1$/Cr(acac)3/AlEt$_3$ = 2/1/400 | 0.94 | 45.6 | 95.9 | 51.7 | 99.2 | 95.0 |
| Example 4 | $I^1$/CrCl$_3$(THF)$_3$MMAO = 2/1/400 | 1.52 | 36.1 | 95.3 | 60.5 | 99.5 | 94.6 |
| Example 5 | $I^1$/Cr(acac)$_3$/MMAO = 2/1/400 | 2.36 | 42.2 | 95.1 | 54.6 | 100 | 94.7 |
| Example 6 | $I^1$/CrCl$_3$(THF)$_3$/MMAO = 2/1/400 | 2.02 | 61.3 | 95.5 | 37.5 | 99.4 | 95.8 |
| Example 7 | $I^1$/Cr(acac)$_3$/MMAO = 2/1/400 | 1.91 | 69.7 | 95.2 | 30.7 | 99.4 | 96.9 |
| Example 8 | $I^1$/Cr(acac)$_3$/MMAO = 2/1/400 | 2.43 | 82.2 | 96.1 | 17.5 | 98.7 | 96.3 |
| Example 9 | $I^1$/Cr(acac)$_3$/MMAO = 2/1/400 | 1.57 | 22.4 | 94.7 | 71.5 | 99.6 | 92.4 |
| Example 10 | $I^1$/Cr(acac)$_3$/MMAO = 2/1/400 | 4.05 | 37.1 | 95.6 | 59.4 | 99.9 | 94.8 |
| Comparative example 1 | D1/Cr(acac)$_3$/MMAO = 2/1/400 | 0.02 | 25.3 | 73.1 | 43.3 | 97.5 | 60.7 |
| Comparative example 2 | D2/Cr(acac)$_3$/MMAO = 2/1/400 | 0.05 | 41.0 | 98.3 | 50.0 | 99.5 | 90.1 |
| Comparative example 3 | D3/Cr(acac)$_3$/MMAO = 2/1/400 | 0.09 | 24.6 | 96.9 | 42.9 | 98.1 | 65.9 |
| Comparative example 4 | D4/Cr(acac)$_3$/MMAO = 2/1/400 | 0.87 | 37.0 | 85.6 | 56.6 | 97.1 | 86.6 |
| Comparative example 5 | D5/Cr(acac)$_3$/MMAO = 2/1/400 | 1.26 | 35.5 | 86.8 | 57.1 | 98.8 | 87.2 |
| Comparative example 6 | D6/Cr(acac)$_3$/MMAO = 2/1/400 | 1.39 | 33.3 | 87.0 | 60.0 | 98.0 | 87.8 |
| Example 11 | $I^1$/Cr(acac)$_3$/MMAO = 2/1/500 | 3.18 | 40.9 | 95.8 | 56.0 | 99.9 | 95.1 |
| Example 12 | $I^1$/Cr(acac)$_3$/MAO = 1.5/1/300 | 0.90 | 76.5 | 95.7 | 23.6 | 99.0 | 96.6 |
| Comparative example 7 | $D^2$/Cr(acac)$_3$/MAO = 1.5/1/300 | 0.04 | 42.3 | 96.8 | 49.1 | 99.5 | 89.8 |
| Example 13 | $I^1$/CrCl$_3$(THF)$_3$/MMAO = 1/1/500 | 2.66 | 62.2 | 95.7 | 36.5 | 99.3 | 95.8 |
| Example 14 | $I^1$/CrCl$_3$(THF)$_3$/MMAO = 1/1/500 | 2.39 | 85.5 | 97.6 | 14.3 | 98.8 | 97.6 |
| Comparative example 8 | D7/CrCl$_3$(THF)$_3$/MMAO = 1/1/500 | 1.80 | 43.5 | 86.9 | 51.1 | 98.9 | 88.3 |
| Comparative example 9 | D8/CrCl$_3$(THF)$_3$/MMAO = 1/1/500 | 1.02 | 75.0 | 97.7 | 19.5 | 97.3 | 92.2 |

Examples 15-19

The ethylene oligomerization was carried out by using the same method as Example 1, except that the halogen-containing compound was replaced with the halogen-containing compounds prepared in preparation examples 3-7. The experimental results were listed in Table 2.

Examples 20-25

The ethylene oligomerization was carried out by using the same method as Example 15, wherein the halogen-containing compound was the halogen-containing compound prepared in preparation example 3. The difference between Examples 20-25 and Example 15 was that the temperature or pressure of the oligomerization reaction was different. Wherein, the polymerization temperature was 50° C. in Example 20, the polymerization temperature was 60° C. in Example 21, the polymerization temperature was 70° C. in Example 22, the polymerization temperature was 90° C. in Example 23, and the polymerization temperature was 30° C. in Example 24, and the pressure of ethylene was controlled to be 5 MPa in Example 25. The experimental results were listed in Table 2.

Example 26

The ethylene oligomerization was carried out by using the same method as Example 11, except that the halogen-containing compound was the halogen-containing compound prepared in preparation example 5. The experimental results were listed in Table 2.

Example 27

The ethylene oligomerization was carried out by using the same method as Example 12, except that the halogen-containing compound was the halogen-containing compound prepared in preparation example 6. The experimental results were listed in Table 2.

Example 28

The ethylene oligomerization was carried out by using the same method as Example 13, except that the halogen-containing compound was replaced with the halogen-containing compound prepared in preparation example 5. The experimental results were listed in Table 2.

Example 29

The ethylene oligomerization was carried out by using the same method as Example 14, except that the halogen-containing compound was replaced with the halogen-containing compound prepared in preparation example 5. The experimental results were listed in Table 2.

35-40 and Example 30 was that the temperature or pressure of the oligomerization reaction was different. Wherein, the polymerization temperature was 50° C. in Example 35, the polymerization temperature was 60° C. in Example 36, the polymerization temperature was 70° C. in Example 37, the polymerization temperature was 90° C. in Example 38, and the polymerization temperature was 30° C. in Example 39, and the pressure of ethylene was controlled to be 5 MPa in Example 40. The experimental results were listed in Table 3.

Example 41

The ethylene oligomerization was carried out by using the same method as Example 11, except that the halogen-containing compound was the halogen-containing compound prepared in preparation example 12. The experimental results were listed in Table 3.

TABLE 2

| Groups | Catalyst composition (molar ratio) | Activity $10^8$ g · mol(Cr)$^{-1}$ · h$^{-1}$ | C6 Selectivity, wt % | Content of 1-hexene in C6, % | C8 Selectivity, wt % | Content of 1-octene in C8, % | Total selectivity of 1-hexene and 1-octene wt % |
|---|---|---|---|---|---|---|---|
| Example 15 | I$^3$/Cr(acac)$_3$/MMAO = 2/1/400 | 2.36 | 33.0 | 97.8 | 62.4 | 99.5 | 94.3 |
| Example 16 | I$^4$/Cr(acac)$_3$/MMAO = 2/1/400 | 1.80 | 35.5 | 98.0 | 59.1 | 99.3 | 93.5 |
| Example 17 | I$^5$/Cr(acac)$_3$/MMAO = 2/1/400 | 2.55 | 29.9 | 98.1 | 65.0 | 99.2 | 93.8 |
| Example 18 | I$^6$/Cr(acac)$_3$/MMAO = 2/1/400 | 2.08 | 34.3 | 97.9 | 60.6 | 99.6 | 93.9 |
| Example 19 | I$^7$/Cr(acac)$_3$/MMAO = 2/1/400 | 1.73 | 31.6 | 98.5 | 61.6 | 99.0 | 92.1 |
| Example 20 | I$^3$/Cr(acac)$_3$/MMAO = 2/1/400 | 2.45 | 38.9 | 97.5 | 55.7 | 99.9 | 93.6 |
| Example 21 | I$^3$/Cr(acac)$_3$/MMAO = 2/1/400 | 2.07 | 56.5 | 97.9 | 38.3 | 99.3 | 93.4 |
| Example 22 | I$^3$/Cr(acac)$_3$/MMAO = 2/1/400 | 1.98 | 64.2 | 97.6 | 31.3 | 99.3 | 93.7 |
| Example 23 | I$^3$/Cr(acac)$_3$/MMAO = 2/1/400 | 2.52 | 75.8 | 98.6 | 17.9 | 98.6 | 92.4 |
| Example 24 | I$^3$/Cr(acac)$_3$/MMAO = 2/1/400 | 1.63 | 20.6 | 97.1 | 73.0 | 99.5 | 92.6 |
| Example 25 | I$^3$/Cr(acac)$_3$/MMAO = 2/1/400 | 4.19 | 34.2 | 98.0 | 60.6 | 99.8 | 94.0 |
| Example 26 | I$^5$/Cr(acac)$_3$/MMAO = 2/1/500 | 3.30 | 29.0 | 97.8 | 66.9 | 99.7 | 95.1 |
| Example 27 | I$^6$/Cr(acac)$_3$/MAO = 1.5/1/300 | 0.85 | 70.5 | 98.1 | 23.8 | 99.1 | 92.8 |
| Example 28 | I$^5$/CrCl$_3$(THF)$_3$/MMAO = 1/1/500 | 3.17 | 52.6 | 98.0 | 43.2 | 99.0 | 94.3 |
| Example 29 | I$^5$/CrCl$_3$(THF)$_3$/MMAO = 1/1/500 | 3.01 | 86.8 | 98.7 | 9.6 | 99.1 | 95.2 |

Examples 30-34

The ethylene oligomerization was carried out by using the same method as Example 1, except that the halogen-containing compounds were replaced with the halogen-containing compounds prepared in preparation examples 8-12, respectively. The experimental results were listed in Table 3.

Examples 35-40

The ethylene oligomerization was carried out by the same method as Example 30, wherein the halogen-containing compound was the halogen-containing compound prepared in preparation example 8. The difference between Examples

Example 42

The ethylene oligomerization was carried out by using the same method as Example 12, except that the halogen-containing compound was the halogen-containing compound prepared in preparation example 11. The experimental results were listed in Table 3.

Example 43

The ethylene oligomerization was carried out by using the same method as Example 13, except that the halogen-containing compound was replaced with the halogen-containing compound prepared in preparation example 10. The experimental results were listed in Table 3.

Example 44

The ethylene oligomerization was carried out by using the same method as Example 14, except that the halogen-containing compound was replaced with the halogen-containing compound prepared in preparation example 10. The experimental results were listed in Table 3.

The preferred embodiments of the present invention have been described in detail above, but the present invention is not limited thereto. A variety of simple variations can be made to the technical solutions of the present invention within the scope of the technical concept of the present invention, including combinations of individual technical features in any other suitable manner, and these simple variations and combinations should also be regarded as the disclosure of the present invention and within the scope of protection of the present invention.

TABLE 3

| Groups | Catalyst composition (molar ratio) | Activity $10^8$ g · mol(Cr)$^{-1}$ · h$^{-1}$ | C6 Selectivity, wt % | Content of 1-hexene in C6, % | C8 Selectivity, wt % | Content of 1-octene in C8, % | Total selectivity of 1-hexene and 1-octene wt % |
|---|---|---|---|---|---|---|---|
| Example 30 | $I^8$/Cr(acac)$_3$/MMAO = 2/1/400 | 2.26 | 33.1 | 98.0 | 62.3 | 99.6 | 94.5 |
| Example 31 | $I^9$/Cr(acac)$_3$/MMAO = 2/1/400 | 1.72 | 35.6 | 98.2 | 59.0 | 99.4 | 93.6 |
| Example 32 | $I^{10}$/Cr(acac)$_3$/MMAO = 2/1/400 | 2.44 | 30.0 | 98.3 | 64.9 | 99.1 | 93.8 |
| Example 33 | $I^{11}$/Cr(acac)$_3$/MMAO = 2/1/400 | 1.99 | 34.4 | 98.1 | 60.5 | 99.5 | 93.9 |
| Example 34 | $I^{12}$/Cr(acac)$_3$/MMAO = 2/1/400 | 2.11 | 34.6 | 98.0 | 61.0 | 99.8 | 94.8 |
| Example 35 | $I^8$/Cr(acac)$_3$/MMAO = 2/1/400 | 2.34 | 39.0 | 97.7 | 55.6 | 99.9 | 93.7 |
| Example 36 | $I^8$/Cr(acac)$_3$/MMAO = 2/1/400 | 1.98 | 56.7 | 98.1 | 38.2 | 99.4 | 93.6 |
| Example 37 | $I^8$/Cr(acac)$_3$/MMAO = 2/1/400 | 1.89 | 64.4 | 97.8 | 31.2 | 99.5 | 94.0 |
| Example 38 | $I^8$/Cr(acac)$_3$/MMAO = 2/1/400 | 2.41 | 76.0 | 98.8 | 17.9 | 98.7 | 92.8 |
| Example 39 | $I^8$/Cr(acac)$_3$/MMAO = 2/1/400 | 1.56 | 20.7 | 97.3 | 72.9 | 99.3 | 92.5 |
| Example 40 | $I^8$/Cr(acac)$_3$/MMAO = 2/1/400 | 4.01 | 34.3 | 98.2 | 60.5 | 99.8 | 94.1 |
| Example 41 | $I^{12}$/Cr(acac)$_3$/MMAO = 2/1/500 | 3.17 | 40.3 | 97.8 | 54.7 | 99.8 | 94.0 |
| Example 42 | $I^{11}$/Cr(acac)$_3$/MAO = 1.5/1/300 | 0.97 | 69.9 | 98.5 | 25.1 | 99.7 | 93.9 |
| Example 43 | $I^{10}$/CrCl$_3$(THF)$_3$/MMAO = 1/1/500 | 2.53 | 58.9 | 98.3 | 36.9 | 99.2 | 94.5 |
| Example 44 | $I^{10}$/CrCl$_3$(THF)$_3$/MMAO = 1/1/500 | 2.25 | 79.9 | 98.0 | 16.3 | 99.1 | 94.4 |

It can be seen from the results in Table 1 that the change in the structure of the catalyst ligand has a significant effect on the catalytic performance. Compared with the catalysts in comparative examples, the catalyst composition according to the present invention has a significantly improved catalytic activity, and can generate a good balance between the catalytic activity and the product selectivity, and decrease the production of by-products such as cycloolefins and cyclized products, demonstrating that the fluorine-containing bridged biphosphine catalyst according to the present invention has better performance.

In addition, during the polymerization reaction, the catalytic system of the catalyst composition according to the present invention initiates quickly and runs smoothly, and can more effectively catalyze the trimerization and tetramerization of ethylene. Wherein, the catalyst composition according to the present invention can maximize ethylene absorption in just a few minutes (within 5 minutes) for 0.5 hours or above. This shows that the catalyst composition according to the present invention has high practicability and broad prospects for industrialization.

The invention claimed is:

1. A halogen-containing compound, represented by a formula I,

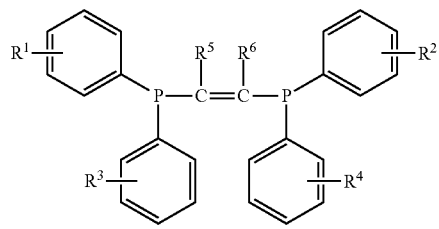

(formula I)

wherein in the formula I, $R^1$, $R^2$, $R^3$, and $R^4$ are the same or different, and each independently is halogen; $R^5$ and $R^6$ are the same or different, and each independently is hydrogen, $C_1$-$C_{12}$ alkyl, $C_3$-$C_{12}$ cycloalkyl, or $C_6$-$C_{20}$ aryl.

2. The halogen-containing compound according to claim 1, wherein in the formula I, both $R^5$ and $R^6$ are hydrogen.

3. The halogen-containing compound according to claim 1, wherein in the formula I, $R^5$ and $R^6$ are the same or different, and each independently is $C_1$-$C_{12}$ alkyl, $C_3$-$C_{12}$ cycloalkyl, or $C_6$-$C_{20}$ aryl;
   or, in the formula I, $R^5$ and $R^6$ are the same or different, and each independently is $C_1$-$C_8$ alkyl, $C_3$-$C_8$ cycloalkyl, or $C_6$-$C_{16}$ aryl;
   or, in the formula I, $R^5$ and $R^6$ are the same or different, and each independently is $C_1$-$C_6$ alkyl, $C_3$-$C_6$ cycloalkyl, or $C_6$-$C_{12}$ aryl;
   or, in the formula I, $R^5$ and $R^6$ are the same or different, and each independently is methyl, ethyl, n-propyl, isopropyl, n-butyl, tert-butyl, isobutyl, n-pentyl, isopentyl, tert-pentyl, cyclopropyl, cyclobutyl, cyclopentyl, cyclohexyl, phenyl, methylphenyl, ethylphenyl, chlorophenyl, or naphthyl;
   or, in the formula I, $R^5$ and $R^6$ are the same or different, and each independently is tert-butyl, cyclohexyl, phenyl, isopropyl, or methyl;
   or, in the formula I, $R^5$ and $R^6$ are the same or different, and each independently is tert-butyl, cyclohexyl, or methyl.

4. The halogen-containing compound according to claim 1, wherein in the formula I, $R^5$ is hydrogen, and $R^6$ is $C_1$-$C_{12}$ alkyl, $C_3$-$C_{12}$ cycloalkyl, or $C_6$-$C_{20}$ aryl;
   or, in the formula I, $R^5$ is hydrogen, and $R^6$ is $C_1$-$C_8$ alkyl, $C_3$-$C_8$ cycloalkyl, or $C_6$-$C_{16}$ aryl;
   or, in the formula I, $R^5$ is hydrogen, and $R^6$ is $C_1$-$C_6$ alkyl, $C_3$-$C_6$ cycloalkyl, or $C_6$-$C_{12}$ aryl;
   or, in the formula I, $R^5$ is hydrogen, and $R^6$ is methyl, ethyl, n-propyl, isopropyl, n-butyl, tert-butyl, isobutyl, n-pentyl, isopentyl, tert-pentyl, cyclopropyl, cyclobutyl, cyclopentyl, cyclohexyl, phenyl, methylphenyl, ethylphenyl, chlorophenyl, or naphthyl;
   or, in the formula I, $R^5$ is hydrogen, and $R^6$ is tert-butyl, cyclohexyl, phenyl, isopropyl, or ethyl;
   or, in the formula I, $R^5$ is hydrogen, and $R^6$ is tert-butyl, cyclohexyl, or phenyl.

5. The halogen-containing compound according to claim 1, wherein $R^1$, $R^2$, $R^3$ and $R^4$ are the same or different, and each independently is chlorine or fluorine;
   or, $R^1$, $R^2$, $R^3$ and $R^4$ are fluorine.

6. The halogen-containing compound according to claim 1, wherein at least one of $R^1$, $R^2$, $R^3$, and $R^4$ is an ortho-substituent;
   or, all of $R^1$, $R^2$, $R^3$ and $R^4$ are an ortho-substituent.

7. The halogen-containing compound according to claim 1, wherein the halogen-containing compound is selected from compounds represented by formulae II and compounds represented by formulae III,

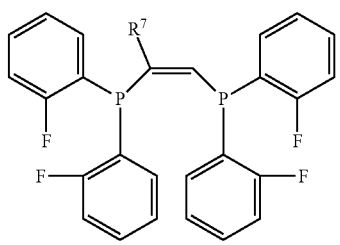

(formula II)

in the formula II, $R^7$ is $C_1$-$C_{12}$ alkyl, $C_3$-$C_{12}$ cycloalkyl, or $C_6$-$C_{20}$ aryl;

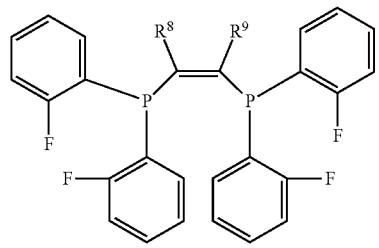

(formula III)

in the formula III, $R^8$ and $R^9$ are the same or different, each independently is $C_1$-$C_{12}$ alkyl, $C_3$-$C_{12}$ cycloalkyl, or $C_6$-$C_{20}$ aryl.

8. The halogen-containing compound according to claim 7, wherein in the formulae II and III, $R^7$, $R^8$ and $R^9$ each independently is $C_1$-$C_8$ alkyl, $C_3$-$C_8$ cycloalkyl, or $C_6$-$C_{16}$ aryl;
   or, in the formulae II and III, $R^7$, $R^8$ and $R^9$ each independently is $C_1$-$C_6$ alkyl, $C_3$-$C_6$ cycloalkyl, or $C_6$-$C_{12}$ aryl;
   or, in the formulae II and III, $R^7$, $R^8$ and $R^9$ each independently is methyl, ethyl, n-propyl, isopropyl, n-butyl, tert-butyl, isobutyl, n-pentyl, isopentyl, tert-pentyl, cyclopropyl, cyclobutyl, cyclopentyl, cyclohexyl, phenyl, methylphenyl, ethylphenyl, chlorophenyl, or naphthyl;
   or, in the formulae II and III, $R^7$, $R^8$ and $R^9$ each independently is tert-butyl, cyclohexyl, phenyl, isopropyl, or ethyl;
   or, in the formula II, $R^7$ is tert-butyl, cyclohexyl, or phenyl;
   or, in the formula III, $R^8$ and $R^9$ each independently is tert-butyl, cyclohexyl, or methyl.

9. An ethylene oligomerization catalyst composition, comprising at least one halogen-containing compound of claim 1, at least one transition metal compound, and at least one cocatalyst.

10. The composition according to claim 9, wherein a molar ratio of the halogen-containing compound to the transition metal compound is 1:0.1-10, or 1:025-2, or 1:0.5-2, and a molar ratio of the halogen-containing compound to the co-catalyst is 1:1-1000, or 1:10-700, or 1:100-500.

11. The composition according to claim 9, wherein the transition metal compound is at least one selected from the group consisting of a chromium compound, a molybdenum compound, an iron compound, a titanium compound, a zirconium compound, and a nickel compound, or at least one selected from the group consisting of chromium acetylacetonate, chromium isooctanoate, tris(tetrahydrofuran)chromium trichloride, and bis(tetrahydrofuran)chromium dichloride, the co-catalyst is an aluminum-containing co-catalyst;
   or, the co-catalyst is an organoaluminum compound;
   or, the co-catalyst is at least one selected from the group consisting of alkyl aluminum, alkoxy aluminum and alkyl aluminum halide;
   or, the co-catalyst is at least one selected from the group consisting of methylaluminoxane, trimethylaluminum, triethylaluminum, triisobutylaluminum, tri-n-hexylaluminum, tri-n-octylaluminum, aluminium diethyl monochloride, aluminium ethyl dichloride, ethylaluminoxane, and modified methylaluminoxane;

or, the co-catalyst is at least one selected from the group consisting of modified methylaluminoxane, methylaluminoxane, and triethylaluminum.

12. An ethylene oligomerization method, comprising a step of contacting ethylene with the catalyst composition according to claim 9.

13. The method according to claim 12, wherein the contacting is carried out in at least one organic solvent, the organic solvent is at least one selected from the group consisting of $C_6$-$C_{12}$ alkane, $C_6$-$C_{12}$ cycloalkane, and $C_6$-$C_{12}$ aromatic hydrocarbon, Or, the organic solvent is at least one selected from the group consisting of methylcyclohexane, heptane, cyclohexane, toluene, and xylene, and wherein the organic solvent is used in an amount that the concentration of the catalyst composition, in terms of a transition metal element in the transition metal compound, is 1-20 μmol/L.

14. The method according to claim 12, wherein the contacting is carried out at a temperature of 0-200° C., or 0-100° C., or 30-90° C., and the pressure of the ethylene is 0.1-20 MPa, or 0.5-10 MPa, or 2-8 MPa.

15. An ethylene trimerization method, comprising a step of contacting ethylene with the catalyst composition according to claim 9 at a temperature of 60° C. or above.

16. The trimerization method according to claim 15, wherein the contacting is carried out in at least one organic solvent, and the organic solvent is at least one selected from the group consisting of $C_6$-$C_{12}$ alkane, $C_6$-$C_{12}$ cycloalkane and $C_6$-$C_{12}$ aromatic hydrocarbon;

or, the organic solvent is at least one selected from the group consisting of methylcyclohexane, heptane, cyclohexane, toluene and xylene, wherein the organic solvent is used in an amount such that the concentration of the catalyst composition in the solvent, in terms of a transition metal element in the transition metal compound, is 1-20 μmol/L, and wherein the pressure of the ethylene is 0.1-20 MPa, or 0.5-5 MPa, or 1-4 MPa, or 2-3 MPa.

17. The trimerization method according to claim 15, wherein the contacting is carried out at a temperature of 60-90° C.

18. An ethylene tetramerization method, comprising a step of contacting ethylene with the catalyst composition according to claim 9 at a temperature of lower than 60° C.

19. The tetramerization method according to claim 18, wherein the contacting is carried out in at least one organic solvent, the organic solvent is at least one selected from the group consisting of $C_6$-$C_{12}$ alkane, $C_6$-$C_{12}$ cycloalkane, and $C_6$-$C_{12}$ aromatic hydrocarbon;

or, the organic solvent is at least one selected from methylcyclohexane, heptane, cyclohexane, toluene and xylene, wherein the organic solvent is used in an amount that the concentration of the catalyst composition in the solvent, in terms of a transition metal element in the transition metal compound, k 1-20 μmol/L, and wherein the pressure of the ethylene is 0.1-20 MPa, or 0.5-8 MPa, or 3-6 MPa, or 4-5 MPa.

20. The tetramerization method according to claim 18, wherein the contacting is carried out at a temperature of 30-50° C.

* * * * *